(12) United States Patent
Fuselier et al.

(10) Patent No.: US 7,771,727 B2
(45) Date of Patent: Aug. 10, 2010

(54) CONJUGATES OF THERAPEUTIC OR CYTOTOXIC AGENTS AND BIOLOGICALLY ACTIVE PEPTIDES

(75) Inventors: Joseph A. Fuselier, New Orleans, LA (US); David H. Coy, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 1267 days.

(21) Appl. No.: 10/506,223

(22) PCT Filed: Mar. 3, 2003

(86) PCT No.: PCT/US03/06657

§ 371 (c)(1),
(2), (4) Date: Jul. 13, 2005

(87) PCT Pub. No.: WO03/074551

PCT Pub. Date: Sep. 12, 2003

(65) Prior Publication Data

US 2006/0009622 A1  Jan. 12, 2006

Related U.S. Application Data

(60) Provisional application No. 60/360,831, filed on Mar. 1, 2002.

(51) Int. Cl.
*A61K 39/00* (2006.01)
*A61K 38/00* (2006.01)
*C12N 9/96* (2006.01)

(52) U.S. Cl. .............. 424/185.1; 514/2; 530/300; 435/188; 424/193.1

(58) Field of Classification Search ............. None
See application file for complete search history.

(56) References Cited

U.S. PATENT DOCUMENTS

| | | | |
|---|---|---|---|
| 4,812,590 A | 3/1989 | Saari | 560/137 |
| 4,904,642 A | 2/1990 | Coy et al. | 514/11 |
| 5,073,541 A | 12/1991 | Taylor et al. | 514/9 |
| 5,411,943 A | 5/1995 | Bogden | 514/16 |
| 5,597,894 A | 1/1997 | Coy et al. | 530/311 |
| 5,620,675 A | 4/1997 | McBride et al. | 424/1.69 |
| 5,633,263 A | 5/1997 | Coy et al. | 530/311 |
| 5,663,306 A | 9/1997 | Aldwin et al. | |
| 5,708,135 A | 1/1998 | Coy et al. | 530/311 |
| 5,750,499 A | 5/1998 | Hoeger et al. | 514/9 |
| 5,753,627 A | 5/1998 | Albert et al. | 514/16 |
| 5,770,687 A | 6/1998 | Hornik et al. | 530/311 |
| 5,948,750 A | 9/1999 | Garsky et al. | |
| 6,017,509 A | 1/2000 | Dean et al. | 424/1.69 |
| 6,051,554 A | 4/2000 | Hornik et al. | 514/11 |
| 6,156,725 A | 12/2000 | Mukherjee et al. | 514/12 |
| 6,326,353 B1 * | 12/2001 | Zalipsky et al. | 514/11 |
| 6,608,026 B1 * | 8/2003 | Wang et al. | 514/2 |
| 2002/0094964 A1 | 7/2002 | Chen et al. | |

FOREIGN PATENT DOCUMENTS

| | | |
|---|---|---|
| EP | 0 296 811 | 12/1988 |
| EP | 1 118 336 | 7/2001 |
| WO | WO 89/04666 | 6/1989 |
| WO | WO 91/01144 | 2/1991 |
| WO | WO 95/03330 | 2/1995 |
| WO | WO 96/39161 | 12/1996 |
| WO | WO 97/19954 | 6/1997 |
| WO | WO-98/37055 * | 8/1998 |
| WO | WO 98/47524 | 10/1998 |
| WO | WO 00/31122 | 6/2000 |
| WO | WO 01/36003 | 5/2001 |
| WO | WO 03/028527 | 4/2003 |

OTHER PUBLICATIONS

Bundgaard, 1991, Pharmaceutical Research, 8, 1238-1242.*
Saari et al., J. Med. Chem. 33(9):2590-2595, 1990.*
Chen et al. US 2002/0094964 A1, published Jul. 18, 2002.
Blower et al., "Iodine-123 Salmon Calcitonin, An Imaging Agent for Calcitonin Receptors: Synthesis, Biodistribution, Metabolism and Dosimetry in Humans," *Eur. J. Nucl. Med.* 25:101-108 (1998).
Chave et al., "Bombesin Family Receptor and Ligand Gene Expression in Human Colorectal Cancer and Normal Mucosa," *Br. J. Cancer* 82:124-130 (2000).
Chen et al., "A Functional Angiotensin II Receptor-GFP Fusion Protein: Evidence for Agonist-Dependent Nuclear Translocation," *Am. J. Physiol. Renal Physiol.* 279:F440-F448 (2000).
Denzler and Reubi, "Expression of Somatostatin Receptors in Peritumoral Veins of Human Tumors," *Cancer* 85:188-198 (1999).
Duncan and Spreafico, "Polymer Conjugates. Pharmacokinetic Considerations for Design and Development," *Clin. Pharmacokinet.* 27:290-306 (1994).
Dubowchik and Walker, "Receptor-Mediated and Enzyme-Dependent Targeting of Cytotoxic Anticancer Drugs," *Pharmacol. Ther.* 83:67-123 (1999).
Evans et al., "Analysis of Somatostatin Receptor Subtype mRNA Expression in Human Breast Cancer," *Br. J. Cancer* 75:798-803 (1997).
Gulec et al., "Antitumor and Antiangiogenic Effects of Somatostatin Receptor-Targeted In Situ Radiation with (111)In-DTPA-JIC 2DL," *J. Surg. Res.* 97:131-137 (2001).
Hornick et al., "Progressive Nuclear Translocation of Somatostatin Analogs," *J. Nucl. Med.* 41:1256-1263 (2000).

(Continued)

*Primary Examiner*—Andrew D Kosar
*Assistant Examiner*—Satyanarayana R Gudibande
(74) *Attorney, Agent, or Firm*—Clark & Elbing LLP

(57) ABSTRACT

The invention features conjugates of therapeutic or cytotoxic agents and biologically active peptides and methods of use thereof.

29 Claims, 2 Drawing Sheets

OTHER PUBLICATIONS

Janson et al., "Nuclear Localization of 111In After Intravenous Injection of [111In-DTPA-D-Phe1]-octreotide in Patients with Neuroendocrine Tumors," *J. Nucl. Med.* 41:1514-1518 (2000).

Kahan et al., "Inhibition of Growth of MX-1, MCF-7-MIII and MDA-MB-231 Human Breast Cancer Xenografts after Administration of a Targeted Cytotoxic Analog of Somatostatin, AN-238," *Int. J. Cancer* 82:592-598 (1999).

Kratz et al., "Drug-Polymer Conjugates Containing Acid-Cleavable Bonds," *Crit. Rev. Ther. Drug Carrier Syst.* 16:245-288 (1999).

Liu and Edwards, "Bifunctional Chelators for Therapeutic Lanthanide Radiopharmaceuticals," *Bioconjug. Chem.* 12:7-34 (2001).

Lukinius et al., "In Vivo Cellular Distribution and Endocytosis of the Somatostatin Receptor -Ligand Complex," *Acta Oncol.* 38:383-387 (1999).

Mariani et al., "Emerging Roles for Radiometabolic Therapy of Tumors Based on Auger Electron Emission," *J. Nucl. Med.* 41:1519-1521 (2000).

Millar et al., "A Novel Mammalian Receptor for the Evolutionarily Conserved Type II GnRH," *Proc. Natl. Sci. USA* 98:9636-9641 (2001).

Monfardini and Veronese, "Stabilization of Substances in Circulation," Bioconjugate Chemistry 9:418-450 (1998).

Morel, "Internalization and Nuclear Localization of Peptide Hormones," *Biochem. Pharmacol.* 47:63-76 (1994).

Neill et al., "A Gonadotropin-Releasing Hormone (GnRH) Receptor Specific for GnRH II in Primates," *Biochem. Biophys. Res. Commun.* 282:1012-1018 (2001).

Plonowski et al., "Inhibition of Metastatic Renal Cell Carcinomas Expressing Somatostatin Receptors by a Targeted Cytotoxic Analogue of Somatostatin AN-238," *Cancer Res.* 60:2996-3001 (2000).

Raynor et al., "Cloned Somatostatin Receptors: Identification of Subtype-Selective Peptides and Demonstration of High Affinity Binding of Linear Peptides," Mol. Pharmacol. 43:844 (1993).

Rypacek et al., "The Renal Excretion and Retention of Macromolecules: The Chemical Structure Effect," *Pflugers Arch.* 392:211-217 (1982).

Sastry, "Biological Effects of the Auger Emitter Iodine-125: A Review. Report No. 1 of AAPM Nuclear Medicine Task Group No. 6," *Med. Phys.* 19:1361-1370 (1992).

Schaer et al., "Somatostatin Receptor Subtypes $sst_1$, $sst_2$, $sst_3$ and $sst_5$ Expression in Human Pituitary, Gastroentero-Pancreatic and Mammary Tumors: Comparison of mRNA Analysis with Receptor Autoradiography," *Int. J. Cancer* 70:530-537 (1997).

Takahashi et al., "Expression of Urotensin II and Urotensin II Receptor mRNAs in Various Human Tumor Cell Lines and Secretion of Urotensin II-Like Immunoreactivity by SW-13 Adrenocortical Carcinoma Cells," *Peptides* 22:1175-1179 (2001).

Vigroux et al., "Cyclization-Activated Prodrugs: N-(Substituted 2-Hydroxyphenyl and 2-Hydroxypropyl)Carbamates Based on Ring-Opened Derivatives of Active Benzoxazolones and Oxazolidinones as Mutual Prodrugs of Acetaminophen," *J. Med. Chem.* 38:3983-3994 (1995).

Wheldon et al., "The Curability of Tumours of Differing Size by Targeted Radiotherapy Using $^{131}$I or $^{90}$Y," *Radiother. Oncol.* 21:91-99 (1991).

Woltering et al., "Somatostatin Analogues Inhibit Angiogenesis in the Chick Chorioallantoic Membrane," *J. Surg Res.* 50:251 (1991).

Yamaoka et al., "Distribution and Tissue Uptake of Poly(Ethylene Glycol) with Different Molecular Weights After Intravenous Administration to Mice," *J. Pharm. Sci.* 83:601-606 (1994).

Yamaoka et al., "Comparison of Body Distribution of Poly(Vinyl Alcohol) with Other Water-Soluble Polymers after Intravenous Administration," *J. Pharm. Pharmacol.* 47:479-486 (1995).

Ingallinella et al., "A New Method for Chemoselective Conjugation of Unprotected Peptides to Dauno- and Doxorubicin," *Bioorganic & Medicinal Chemistry Letters* 11:1343-1346, 2001.

Fuselier et al., "Specific Targeting of Camptothecin and Combretastatin to Tumor Cells Using Cleavable High Affinity Somatostatin Agonist Vectors," *Proceedings of the American Association for Cancer Research Annual Meeting* 43: 1157, 2002.

Cai et al., "Superactive octapeptide somatostatin analogs containing tryptophan at position 1," *Proc. Natl. Acad. Sci. USA* 84(8):2502-2506, 1987.

Cai et al., "Synthesis and biological activity of highly potent octapeptide analogs of somatostatin," *Proc. Natl. Acad. Sci. USA* 83(6):1896-1900, 1986.

Hoffman et al., "Synthesis and characterization of $^{105}$Rh labelled bombesin analogues: enhancement of GRP binding affinity utilizing aliphatic carbon chain linkers," *J. Labelled Cpd. Radiopharm.* 40:490-492, 1997.

Kiaris et al., "Regression of U-87 MG human glioblastomas in nude mice after treatment with a cytotoxic somatostatin analog AN-238," *Clin. Cancer Res.* 6(2):709-717, 2000.

Kiaris et al., "A targeted cytotoxic somatostatin (SST) analogue, AN-238, inhibits the growth of H-69 small-cell lung carcinoma (SCLC) and H-157 non-SCLC in nude mice," *Eur. J. Cancer* 37(5):620-628, 2001.

Koppan et al., "Targeted cytotoxic analogue of somatostatin AN-238 inhibits growth of androgen-independent Dunning R-3327-AT-1 prostate cancer in rats at nontoxic doses," Cancer Res. 58(18):4132-4137, 1998.

Nagy et al. "Selective coupling of methotrexate to peptide hormone carriers through a gamma-carboxamide linkage of its glutamic acid moiety: benzotriazol-1-yloxytris(dimethylamino)phosphonium hexafluorophosphate activation in salt coupling," *Proc. Nati. Acad. Sci. USA* 90(13):6373-6376, 1993.

Plonowski et al., "Inhibition of metastatic renal cell carcinomas expressing somatostatin receptors by a targeted cytotoxic analogue of somatostatin AN-238," *Cancer Res.* 60(11):2996-3001, 2000.

Plonowski et al., "Inhibition of PC-3 human androgen-independent prostate cancer and its metastases by cytotoxic somatostatin analogue AN-238," Cancer Res. 59(8):1947-1953, 1999.

Plonowski et al., "Inhibition of the UCI-107 human ovarian carcinoma cell line by a targeted cytotoxic analog of somatostatin, AN-238," *Cancer* 92(5):1168-1176, 2001.

Plonowski et al., "In vivo inhibition of PC-3 human androgen-independent prostate cancer by a targeted cytotoxic bombesin analogue, AN-215," *Int J. Cancer* 88(4):652-657, 2000.

Saari et al., "Cyclization-activated prodrugs. Basic esters of 5-bromo-2'-deoxyuridine," *J. Med. Chem.* 33(9):2590-2595, 1990.

Smith et al., "Radiochemical investigations of $^{177}$Lu-DOTA-8-Aoc-BBN[7-14]NH$_2$: a new gastrin releasing peptide receptor (GRPr) targeting radiopharmaceutical," *J. Labelled Cpd. Radiopharm.* 44:S706-S708, 2001.

Srkalovic et al., "Evaluation of receptors for somatostatin in various tumors using different analogs," J. Clin. Endocrinol. Metab. 70(3):661-669, 1990.

Supplemental European Search Report for European Patent Application No. 02 775 944.8, dated Jun. 16, 2009.

GenBank Accession No: 720473A (1992).
GenBank Accession No: AAB22264 (1993).
GenBank Accession No: 0601216A (1996).

O'Donnell et al, "Structure-activity studies of vasoactive intestinal polypeptide" J. Biol. Chem. 266:6389-6392, 1991.

* cited by examiner

CONJUGATES OF THERAPEUTIC OR CYTOTOXIC AGENTS AND BIOLOGICALLY ACTIVE PEPTIDES

CROSS-REFERRNCE TO RELATED APPLICATIONS

This application is the National Stage of International Application No. PCT/US03/06657 filed Mar. 3, 2003, which was published in English under PCT Article 21(2), and which claims benefit of U.S. Provisional Application No. 60/360,831, filed Mar. 1, 2002, each of which is hereby incorporated by reference.

FIELD OF THE INVENTION

The invention relates to conjugates of therapeutic or cytotoxic agents and biologically active peptides and uses therof.

BACKGROUND OF THE INVENTION

The use of carbamate compounds as prodrugs is well known. Carbamate compounds are well suited for prodrug design because they can be used to regenerate the parent drug whether the point of connection to a vector molecule is a hydroxyl group or an amine. Carbamate prodrugs based on intramolecular cyclizations have been reported since the late 1980s. For example, U.S. Pat. No. 4,812,590 (which corresponds to EP 0 296 811) discloses derivatives of 4-hydroxyanisole carbamate as prodrugs for the delivery and concentration of 4-hydroxyanisole in melanomas. Vigroux et al. (J. Med. Chem. 38, 3983-3994, 1995) disclose prodrugs of acetaminophen which incorporate N-(substituted 2-hydroxyphenyl)- and N-(substituted 2-hydroxypropyl)carbamates.

An optimal prodrug design is one in which the drug is conjugated to a biologically active vector such that the conjugate is completely stable in circulation, but releases the therapeutic agent cleanly when internalized into target cells. Various types of linker technologies attempt to achieve this goal by different chemical means. Two types of biodegradation phenomena, passive hydrolysis and enzymatic hydrolysis, are typically considered. Passive hydrolysis occurs when the molecule degrades by simple chemical decomposition; esters, carbonates, amides and urethanes are all susceptible to varying degrees of hydrolysis with the following order of stability at basic pH: urethanes >amides>carbonates>esters. Enzymatic hydrolysis occurs in plasma circulation as well as upon internalization. If the desired result is to transport the conjugate to the target cell, it is desirable that the conjugate be very resistant to plasma enzymes that could degrade the complex en route. Commonly used ester derivatives are a particularly poor choice of linker because peripherally circulating compound is rapidly attacked by ubiquitous esterases.

Another linker strategy capitalizes on pH differences existing between the inside and outside of cells. Lysosomes, which are responsible for degrading molecules within cells, have a pH of 4-6, while plasma and extracellular fluid has a pH of 7.4. A linker that is designed to degrade at pH 5, but is stable at pH 7, may be useful for delivering the conjugate to cells, assuming that the conjugate does not undergo passive or enzymatic hydrolysis in plasma. However, this linker strategy is not optimal for peptide conjugates because most of the work-up and purification of synthetic peptides is done in acidic media.

Still other chemical linkers attempt to capitalize on specific enzymes found in lysosomes. For example, many peptide sequences are stable in plasma but are specifically cleaved by lysosomal enzymes.

The toxic side effects of many of these therapies, as well as standard treatments of neoplastic disease, effectively limit the amount of active agent that may be administered to a patient. Additionally, many active agents cause organ-specific toxicities, further limiting the dose that may be delivered to the target tissue. For instance, the cardiotoxicity of many anthracycline family members reduces the maximum therapeutic dose available for this group of chemotherapeutic agents. Targeted drug delivery of various therapeutic agents can lower toxicity in normal tissue and increase the efficacy of treatment by allowing concentrated localized effects on specific tissues.

Somatostatin, bombesin, and other biologically active peptide analogs have been used to detect tumor cells that overexpress receptors specific for these peptides (see, e.g., Denzler and Reubi, Cancer 85(1):188-198, 1999). Moreover, somatostatin, bombesin and many other biologically active peptide agonist analogs are rapidly internalized after binding to their receptors (see, e.g., Lukinius et al, Acta Onc. 38:383-387, 1999). This internalization of the peptide analogs may result in translocation to the cell nucleus (Chen et al., Am. J. Physiol. Renal Physiol., 279: F440-F448, 2000).

Somatostatin analogs bind specific somatostatin receptor subtypes that are present on the surface of specific normal or diseased tissues. Somatostatin receptors are up-regulated in specific diseased tissues, including inflammatory bowel diseases, rheumatoid arthritis, and a variety of tumor types, as well as blood vessels supplying many tumors (Denzler and Reubi, Cancer, 85:4188-198, 1999). Similarly, receptors specific for another biologically active peptide, Substance P, can be up-regulated in various diseases.

At least five somatostatin receptors subtypes have been characterized, and tumors can express various receptor subtypes. (Shaer, et al., Int. 3. Cancer 70:530-537, 1997). Naturally occurring somatostatin and its analogs exhibit differential binding to these receptor subtypes, allowing precise targeting of a peptide analog to specific diseased tissues.

The physical and chemical properties of many cytotoxic agents make drug conjugation to biologically active peptides, such as somatostatin and bombesin, problematic. For example, the drug may reduce the specificity of binding or the biological activity of the peptide analog, limiting its effectiveness as a targeting agent. Additionally, therapeutic and cytotoxic agents may have chemical properties that promote accumulation of drug-peptide analogs in certain organs, increasing toxicity and reducing efficacy. Effective means to link cytotoxic agents to a targeting agent such as a biologically active peptide or an antibody, while retaining the activity of each component are needed to maximize therapeutic effects, while minimizing toxicity.

SUMMARY OF THE INVENTION

The invention features conjugates of a therapeutic agent or a cytotoxic agent and a targeting moiety. In particular, the invention features conjugates having a cleavable chemical linker which reduces the release of therapeutic or cytotoxic agent in circulation, thereby rendering the active agent component of the conjugate more readily internalized by a cell, and more readily subject to active control of release rate inside the cell.

Accordingly, in one aspect, the present invention features biologically active peptides conjugated to chemical compounds through a carbamate linkage. Conjugates of the present invention provide numerous advantages, such as retention of the biological activity of the peptide, enhanced stability of the conjugate in plasma, and intracellular release of the attached compound. Preferred peptides for use with conjugates of the invention include somatostatin, somatostatin analogs, bombesin, bombesin analogs, KiSS peptides and analogs, urotensin II peptides and analogs, GnRH I and II peptides and analogs, octreotide, depreotide, vapreotide, vasoactive intestinal peptide (VIP), cholecystokinin (CCK), insulin-like growth factor (IGF), RGD-containing peptides, melanocyte-stimulating hormone (MSH) peptide, neurotensin, calcitonin, peptides from complementarity determining regions of an antitumor antibody, glutathione, YIGSR (SEQ ID NO. 42; leukocyte-avid peptides, e.g., P483H, which contain the heparin-binding region of platelet factor-4 (PF-4) and a lysine-rich sequence), atrial natriuretic peptide (ANP), β-amyloid peptides, delta-opioid antagonists (e.g., ITIPP(psi)), annexin-V, endothelin, interleuking (IL)-1, IL-1ra, IL-2, and IL-8, leukotriene B4 (LTB4), chemotactic peptides (e.g., N-formyl-methionyl-leucyl-phenylalanine-lysine (fMLFK; SEQ ID NO. 41)), GP IIb/IIIa receptor antagonists (e.g., DMP444), epidermal growth factor, human neutrophil elastase inhibitor (e.g., EPI-HNE-2 and EPI-HNE-4), plasmin inhibitor, antimocrobial peptides, apticide (e.g., P280 and P274), thrombospondin receptor (including analogs such as TP-1300), bitistatin, pituitary adenylyl cyclase type I receptor (PAC1), fibrin α-chain, and derivatives and analogs thereof. Also included are peptides derived from a phage display library, and conservative substitutions thereof, that are targeted to a cell or tissue in the body of a mammal (e.g., diseased tissue, such as a tumor or a proliferative angiogenic blood vessel; see, e.g., Aina et al., Biopolymers 66:184-199, 2002). Such peptides are useful for specifically targeting therapeutic agents and cytotoxic agents to a cell, such as a cancer cell, or to a tissue in the body of a mammal (e.g., the delivery of anti-apoptotic drugs to cardiac or brain tissue), or to selectively target white blood cells or tubercles infected with tuberculosis. For example, when somatostatin or bombesin is used as the biologically active peptide in a conjugate of the invention, the therapeutic or cytotoxic agent may be targeted to a cancer cell that expresses a somatostatin receptor or a bombesin receptor. The invention also features antibodies (e.g., a monoclonal antibody) or a fragment thereof, that can be linked to the conjugate of the invention. As discussed above with respect to peptides, when an antibody is incorporated in a conjugate of the invention, the therapeutic or cytotoxic agent may be targeted to specific antibody binding sites.

Conjugates of the first aspect of the invention have the following general formula:

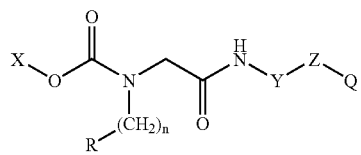

wherein

X is a cytotoxic agent or therapeutic agent;

n is an integer from 0 to 6, wherein $(CH_2)_n$ is substituted or unsubstituted, a straight or branched chain, or is an alkyl, alkenyl, alkynyl, cyclic, heterocyclic, aromatic, or heteroaromatic group;

R is $N(R_1R_2)$, $OR_1$, or $SR_1$ where $R_1$ and $R_2$ are, independently, hydrogen or a lower alkyl group;

Y is an hydrophilic spacer sequence, or is omitted;

Z is a linking peptide, or is omitted; and

Q, when present, is a targeting moiety.

In this and the other aspects of the invention, the alkyl group preferably contains 1-8 carbon atoms; the alkenyl group preferably contains 1-X carbon atoms; the alkynyl group contains 1-X carbon atoms; the cyclic group contains . . .

A second aspect of the invention features a conjugate having the formula:

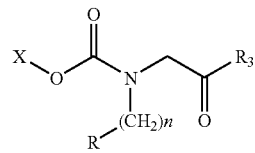

wherein

X is a cytotoxic agent or therapeutic agent;

n is an integer from 0 to 6, wherein $(CH_2)_n$ is substituted or unsubstituted, a straight or branched chain, or is an alkyl, alkenyl, alkynyl, cyclic, heterocyclic, aromatic, or heteroaromatic group;

R is $N(R_1R_2)$, $OR_1$, or $SR_1$ where $R_1$ and $R_2$ are, independently, hydrogen or a lower alkyl group, and wherein $R_3$ is a $NH(CH_2)mSH$ group (where m=2 to 6), a D or L cysteine, a benzophenone (e.g., p-benzoyl-phenylalanine), or an OH group. A conjugate compound having this formula can be used to link to a peptide, protein, or antibody through the thiol, carboxylate, or photoactive benzophenone containing $R_3$ group. In addition, a peptide or protein can be easily prepared by synthesizing the peptide or protein directly onto the compound. For example, the compound can be provided such that the R group is a tBoc protected primary or secondary amino group, and can be added to the peptidyl resin as described in the examples provided below. Peptides, proteins, and antibodies can also be attached to the compound through the use of known thiol-reactive chemical reactions when the $R_3$ group contains a thiol group, or by a photoreactive reaction when $R_3$ contains a benzophenone moiety (see, e.g., Greg T. Hermanson, "Bioconjugate Techniques" p. 146-152, 1996).

In preferred embodiments of all aspects of the invention, X is a cytotoxic agent selected from camptothecin, homocamptothecin, colchicine, combretastatin, dolistatin, doxorubicin, methotrexate, podophyllotoxin, rhizoxin, rhizoxin D, a taxol, paclitaxol, CC1065, or a maytansinoid and derivatives and analogs thereof. For example, the cytotoxic agent camptothecin is linked through its single free hydroxyl group to a carbamate linker. In these embodiments of the invention, n is preferably 2 and R is preferably $NH_2$.

Y is an hydrophilic spacer sequence that may be, preferably, a peptide that increases the biodistribution of the conjugate, or a hydrophilic polymer. For example, Y may be a peptide sequence that increases the hydrophilic biodistribution of the biologically active peptide conjugate. In a preferred embodiment, Y has the formula $U(V-V)_n$, wherein U is D-Pro, L-Pro, D-4-OH-Pro, L-4-OH-Pro, Sarcosine, Lys, Orn, Dab, Dap, 4-$NH_2$-Phe, or ($NH_2$—$(CH_2)_m$—COOH), where m=2-10, inclusive, or is deleted; each V is independently selected from the group consisting of: D-Ser, L-Ser, D-Thr, L-Thr, D-Gln, L-Gln, D-Asn, L-Asn, D-4-OH-Pro, or L-4-hydroxy-Pro; and n=1-50, inclusive. In another preferred embodiment, each V is independently D-Ser or L-Ser. In another preferred embodiment, at least one V is a D-amino acid.

Y may be a hydrophilic polymer. For example, Y may be polyethylene glycol, polyvinyl acetate, polyvinyl alcohol, HPMA (N-(2-hydroxypropyl)methacrylamide) or HPMA copolymers, α, β-poly(N-hydroxyethyl)-DL-aspartamide (PHEA), or α, β-poly(N-hydroxypropyl)-DL-aspartamide.

Z is a linking peptide that preserves at least fifty percent of the biological activity of Q, when Z is bonded to Q through the terminal or side-chain amino group of Q. Generally, Z may be a peptide of 2, 3, 4, or 5 residues. Z has the formula: A-B-C-E-F, where A is D-Lys, D-Tyr, D-Ser, or L-Ser, or deleted; B is D-Lys or D-Tyr, or is deleted; C is Lys, Ser, hSer, Thr, Nle, Abu, Nva, (2,3, or 4) 3-pyridyl-Ala (Pal), Orn, Dab, Dap, 4-NH$_2$-Phe, D-4-OH-Pro, or L-4-OH-Pro, or is deleted; E is D-Lys, D-Tyr, D-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; and F is D-Lys, D-Tyr, D-Ser, L-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; provided that when A, B, C, and E are Tyr, Tyr, Lys, and Tyr, respectively, F is not Lys; and when A, B, C, and E, are Lys, Tyr, Lys, and Tyr, respectively, F is not Tyr or Lys; and when A and B are deleted, and C and E are Lys and Tyr, respectively, F is not Tyr or Lys (SEQ ID NO: 45-48). In some peptides, it may be preferable that Z is absent.

In other embodiments, Z has the formula (when A, B, and C are deleted):

E-F where E is D-Lys, D-Tyr, D-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; and F is D-Lys, D-Tyr, D-Ser, L-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln.

In preferred embodiments, Z is D-Ser-Nle-D-Ser-D-Ser (SEQ ID NO: 1), D-Ser-Lys-D-Ser-D-Ser (SEQ ID NO: 2), D-Ser-Lys-D-Tyr-D-Tyr (SEQ ID NO: 3), D-Ser-Lys-D-Tyr-D-Ser (SEQ ID NO: 4), D-Ser-Ser-D-Lys-D-Ser (SEQ ID NO: 5), D-Ser-Ser-D-Lys-Ser (SEQ ID NO: 5), D-Ser-Nle-D-Tyr-D-Ser (SEQ ID NO: 6), D-Ser-Pal-D-Tyr-D-Ser (SEQ ID NO: 7), D-Ser-Thr-D-Tyr-D-Ser (SEQ ID NO: 8), Lys-D-Ser-D-Ser (SEQ ID NO: 9), Ser-D-Lys-D-Ser (SEQ ID NO: 10), Ser-D-Lys-Ser (SEQ ID NO: 10), Nle-D-Tyr-D-Ser (SEQ ID NO: 11), Lys-D-Tyr-D-Ser (SEQ ID NO: 12), Pal-D-Lys-D-Ser (SEQ ID NO: 13), Thr-D-Tyr-D-Ser (SEQ ID NO: 14), D-Ser-D-Lys, D-Ser-D-Tyr, D-Lys-D-Lys, D-Lys-D-Tyr, or D-Tyr-D-Lys.

Q is a targeting moiety, such as a biologically active peptide or phage derived peptides. In preferred embodiments, Q is a peptide, such as somatostatin, a somatostatin analog, bombesin, a bombesin analog, or an antibody, such as a monoclonal antibody. Preferred biologically active peptide or targeting moieties are internalized by select cells via an active internalization process, such as when binding to a G-protein coupled receptor or somatostatin type 2 receptors (SSTR2).

Another aspect of the invention features a method for the treatment of a disease or modification of a biological function. The method includes administering to a warm-blooded animal in need thereof, e.g., a human, a therapeutically effective or biological function modifying amount of a conjugate of the invention. One of skill in the art will recognize that the particular conjugate used will depend on the disease state to be treated or the biological system to be modified. In particular, one skilled in the art will be able to select a particular targeting moiety and cytotoxic or therapeutic agent to prepare a conjugate of the invention which has specificity for the treatment of the disease or is able to modify the biological function desired. In preferred embodiments, the disease is a tumor of the lung, breast, brain, eye, prostate or colon or a tumor of neuroendocrine origin (e.g., carcinoid syndrome). The disease is also a condition that results from or causes proliferation of angiogenic blood vessels.

By "administration" or "administering" is meant a method of giving a dosage of a pharmaceutical composition to a mammal, where the method is, e.g., topical, oral, intravenous, intraperitoneal, or intramuscular. The preferred method of administration can vary depending on various factors, e.g., the components of the pharmaceutical composition, site of the potential or actual disease and severity of disease.

In the generic descriptions of compounds of this invention, the number of atoms of a particular type in a substituent group is generally given as a range. For example, an alkyl group containing from 1 to 8 carbon atoms or $C_{1-8}$ alkyl. Reference to such a range is intended to include specific references to groups having each of the integer number of atoms within the specified range. For example, an alkyl group from 1 to 8 carbon atoms includes each of $C_1$, $C_2$, $C_3$, $C_4$, $C_5$, $C_6$, $C_7$, and $C_8$. A $C_{1-8}$ heteroalkyl, for example, includes from 1 to 8 carbon atoms in addition to one or more heteroatoms. Other numbers of atoms and other types of atoms may be indicated in a similar manner.

As used herein, "alkyl", is intended to include aliphatic branched or straight chain hydrocarbon group and combinations thereof. An alkyl is optionally substituted with one or more substituents which may be the same or different. An alkyl group contains 1 to 20 carbon atoms, preferably 1 to 8 carbon atoms. Examples include methyl, ethyl, n-propyl, n-butyl, isobutyl, sec-butyl, tert-butyl, pentyl, isoamyl, hexyl, octyl and the like. By "lower alkyl" is meant a branched or straight chain alkyl group having fewer than 11 carbon atoms, preferably a $C_1$-$C_8$ alkyl. By "lower alkylamide" is meant a lower alkyl group as described above substituted with one or more amide-containing groups. As used herein, the terms "alkyl" and the prefix "alk-" can also refer to cyclic groups, i.e., cycloalkyl and cycloalkenyl groups. Cyclic groups can be monocyclic or polycyclic and preferably have from 3 to 8 ring carbon atoms, inclusive.

The term "alkenyl", alone or in combination, means a straight-chain or branched-chain hydrocarbon having one or more double bonds and containing from 2 to 20 carbon atoms, preferably from 2 to about 8 carbon atoms. The term "alkynl", alone or in combination, means a straight-chain or branched-chain hydrocarbon having one or more triple bonds and containing from 2 to about 20 carbon atoms, preferably from 2 to 8 carbon atoms.

By "heteroalkyl" is meant a branched or unbranched group in which one or more methylenes (—CH$_2$—) are replaced by nitrogen, oxygen, sulfur, carbonyl, thiocarbonyl, phosphoryl, sulfonyl, or NR, where R is an alkyl. Some examples include tertiary amines, ethers, thioethers, amides, thioamides, carbamates, thiocarbamates, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted.

By "analog" is meant a molecule that differs from, but is structurally, functionally, and/or chemically related to the reference molecule. The analog may retain the essential properties, functions, or structures of the reference molecule. Most preferably, the analog retains at least one biological function of the reference molecule. Generally, differences are limited so that the structure or sequence of the reference molecule and the analog are similar overall. A peptide analog and its reference peptide may differ in amino acid sequence by one or more substitutions, additions, and/or deletions, in any combination. A substituted or inserted amino acid residue may or may not be one encoded by the genetic code of the peptide analog. An analog of a peptide or polypeptide may be naturally occurring, such as an allelic variant, or it may be a variant that is not known to occur naturally. Non-naturally occurring analogs of peptides may be made by direct synthesis, by modification, or by mutagenesis techniques.

By "biologically-active peptide" is meant any naturally occurring, modified, or synthetic peptide that is involved in a biological process or function. Examples of biologically active peptides include, but are not limited to: hormones, growth factors, neurotransmitters, antigens, antibodies, or fragments thereof.

The term "bombesin peptide" is meant bombesin, or an analog thereof, having at least one biological activity of native bombesin; preferably, this activity is the ability to specifically bind to one or all of the three known bombesin receptor subtypes on a bombesin receptor-bearing cell. Bombesin analogs include, but are not limited to, peptides selected from the group containing the octapeptide G-Trp-H-I-His-J-K-NHV (SEQ ID NO: 15), wherein G is Gln, Asn, Nle, or Nva; H is Ava, Gly, Leu, Val, Ile, Nle, or Nva; I is β-Ala, 4-aminobutyric acid, Gly, Ala, D-Ala, N-Me-Ala, or N-Me-D-Ala; J is Phe, Tyr, 4-Cloro-Phe, 4-Fluoro-Phe, 4-Bromo-Phe, 4-$NO_2$-Phe, Ala, Gly, Leu, Val, Ile, Nle, or Nva; K is Met, Phe, Tyr, 4-Cloro-Phe, 4-Fluoro-Phe, 4-Bromo-Phe, 4-$NO_2$-Phe, Ala, Gly, Leu, Val, Ile, Nle, or Nva; and N represents an amide or a N-alkylamide and V is H or a lower alkylamide.

By "cyclic" is meant a hydrocarbon group having from 3 to 10 carbons and more preferably from 3 to 6 carbons.

By "cytotoxic agent" is meant any naturally-occurring, modified, or synthetic compound that is toxic to tumor cells. Such agents are useful in the treatment of neoplasms, as well as inflammatory diseases, autoimmune disorders, and in the treatment of other symptoms or diseases characterized by cell proliferation or a hyperactive cell population. Cytotoxic agents include, but are not limited to, alkylating agents, antibiotics, antimetabolites, tubulin inhibitors, topoisomerase I and II inhibitors, hormonal agonists or antagonists, or immunomodulators. Cytotoxic agents may be cytotoxic when activated by light or infrared (Photofrin, IR dyes; Nat. Biotechnol. 19(4):327-331, 2001), may operate through other mechanistic pathways, or be supplementary potentiating agents.

By "hydrophilic biodistribution" is meant the affinity of the peptide agents of the invention for the bodily fluids of a subject administered the peptide agents (e.g., blood, cerebrospinal fluid, urine, or other bodily fluids), such that the peptide agents distribute throughout the body of the subject, but are rapidly secreted in the urine via the kidney, while avoiding uptake by peripheral organs such as liver, gall bladder, and kidney proximal tubules.

By "hydrophilic polymer" is meant a naturally-occurring or synthetic water-soluble polymer optionally modified that alters the biodistribution of a peptide agent of the invention. Examples of such polymers include, but are not limited to poly(ethylene glycol) (PEG), poly(vinyl alcohol) (PVA), polyvinyl acetate, dextran, hydroxyethyl starch, gelatin, PVP, PHPMA, α, β-poly[N(2-hydroxyethyl)-DL-aspartamide (PHEA), polysuccinamide (PSI), α, β-poly(N-hydroxypropyl)-DL-aspartamide, etc. These polymers may be modified by, for example, succinylation (negative charge), partial hydrolysis of PSI (carboxylic groups), or reaction with compounds to add amino- or carboxyl-containing groups, etc. Such optional modifications may increase or change the hydrophilicity of the polymer, or enable coupling to the peptide or cytotoxic or therapeutic agent of the invention. Such polymers and modifications are known in the art and are described in, for example, Yamoaka et al., J. Pharmacol. Sci. 83:601-606, 1994; Rypacek et al., Pflugers Arch. 392:211-217, 1982; Yamoaka et al., J. Pharm. Pharmacol. 47:479-486, 1995; Francesco, Bioconjugate Chemistry 9(4):418-450, 1998; Duncan and Spreafico, Clin. Pharmacokinet. 27(4): 290-306,1994; each of which is hereby incorporated by reference in its entirety.

By "hydrophilic spacer sequence" is meant an hydrophilic peptide or hydrophilic polymer that increases biodistribution of a compound of the invention, such as by inhibiting peripheral accumulation and/or promoting renal clearance. Examples of hydrophilic spacer sequences for use with the present invention are provided herein.

By "peptide" is meant any polypeptide, peptide (including cyclic or branched peptides), or protein comprising two or more amino acids joined to each other by peptide bonds or modified peptide bonds. As used herein, peptide refers to short chains, commonly referred to as peptides, oligopeptides or oligomers, and to longer chains, up to about 100 residues in length. Peptides may contain amino acids other than the 20 gene-encoded amino acids, and linkages other than peptide bonds. Peptides include amino acid sequences modified either by natural processes, or by chemical modification techniques that are well known in the art. Modifications may occur anywhere in a polypeptide, including the peptide backbone, the amino acid side-chains, and the amino or carboxyl termini.

The notations used herein for the peptide amino acid residues are those abbreviations commonly used in the art. The less common abbreviations Abu, Ava, β-Ala, hSer, Nle, Nva, Pal, Dab, and Dap stand for 2-amino-butyric acid, amino valeric acid, beta-aminopropionic acid, homoserine, norleucine, norvaline, (2, 3, or 4) 3-pyridyl-Ala, 1,4-diaminobutyric acid, and 1,3-diaminopropionic acid, respectively. In all aspects of the invention, it is noted that when amino acids are not designated as either D- or L-amino acids, the amino acid is either an L-amino acid or could be either a D- or L-amino acid, unless the context requires a particular isomer.

By "somatostatin peptide" is meant a somatostatin, or an analog thereof, having at least one biological activity of native somatostatin; preferably, this activity is the ability to specifically bind to a somatostatin receptor on a somatostatin receptor-bearing cell. Many such analogs having biological activity are known and have been described, for example, in Hornik et al., U.S. Pat. No. 5,770,687; Coy et al., U.S. Pat. No. 5,708,135; Hoeger et al., U.S. Pat. No. 5,750,499; McBride et al., U.S. Pat. No. 5,620,675; Coy et al., U.S. Pat. No. 5,633, 263; Coy et al., U.S. Pat. No. 5,597,894; Taylor et al., U.S. Pat. No. 5,073,541; Coy et al., U.S. Pat. No. 4,904,642; Dean, U.S. Pat. No. 6,017,509; Hoffman et al., WO 98/47524; and A. E. Bogden, U.S. Pat. No. 5,411,943, each of which is hereby incorporated by reference in its entirety.

By "targeting moiety" is meant any molecule that specifically binds or reactively associates or complexes with a receptor or other receptive moiety associated with a given target cell population. This cell reactive molecule, to which the drug reagent is linked via the linker in the conjugate, can be any molecule that binds to, complexes with or reacts with the cell population sought to be therapeutically or otherwise biologically modified and, which possesses a free reactive amine group or can be modified to contain a such an amine group.

The cell reactive molecule acts to deliver the conjugate, and, thus, the cytotoxic or therapeutic agent to the particular target cell population with which the ligand reacts. Such molecules include, but are not limited to, large molecular weight proteins (generally greater than 10,000 daltons) such as, for example, antibodies, smaller molecular weight proteins (generally, less than 10,000 daltons), polypeptide or peptide ligands, and non-peptidyl ligands.

By "therapeutic agent" is meant any compound that is used in the detection, diagnosis or treatment of human disease. Such compounds may be naturally-occurring, modified, or synthetic. Therapeutic agents may promote or inhibit any biological process implicated in a human disease pathway. Preferred disease targets include, but are not limited to, inflammatory bowel disease, rheumatoid arthritis, neoplastic cells apoptosis, cardiac tissues, or aberrantly proliferating cells, carcinoid syndrome, acromegaly, tuberculosis, and angiogenesis that causes inappropriate proliferation of blood vessels (e.g., macular degeneration which results from excess angiogenesis in the eye). A therapeutic agent may be, for example, antineoplastic, including cytotoxic. Antineoplastic agents may be alkylating agents, antibiotics, antimetabolites, hormonal agonists or antagonists, tubulin inhibitors, topoisomerase I and II inhibitors, anti- or pro-apoptotic agents, or immunomodulators. Antineoplastic agents may operate through other mechanistic pathways, or antineoplastic agents may be supplementary potentiating agents.

By "treating" is meant administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to ameliorate the disease and improve the patient's condition. Thus, in the claims and embodiments, treating is the administration to a mammal either for therapeutic or prophylactic purposes.

DETAILED DESCRIPTION OF THE INVENTION

Figure 1:
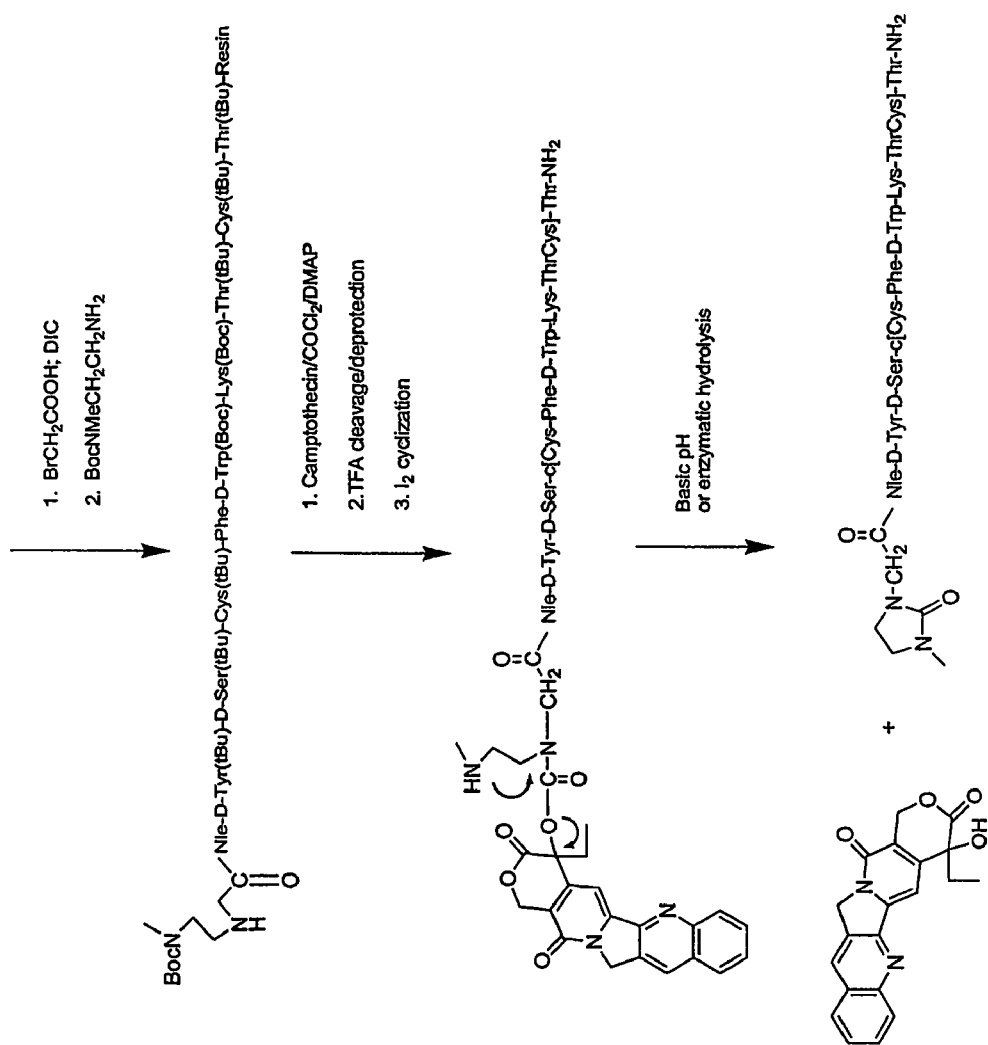
FIG. 1 is a diagram demonstrating the on-resin synthesis of a BINAR group-containing somatostatin analogue and attachment of camptothecin via a carbamate linking group followed by removal from the resin to give compound 2(SEQ ID NO: 43). Basic conditions or enzymatic attack results in nucleophile-assisted release of free camptothecin (SEQ ID NO: 44).

The present invention features conjugates of cytotoxic or therapeutic agents and biologically peptides. These conjugates provide many advantages for the administration of such cytotoxic or therapeutic agents. Conjugates of the invention may be directed to target sites or specific cells, resulting in effective internalization of the cytotoxic or therapeutic agent In addition, conjugates of the invention exhibit reduced release of cytotoxic or therapeutic agent in circulation. Conjugates of the invention may be modified as desired to adjust the release of cytotoxic or therapeutic agent Conjugates of the invention have the following general formula:

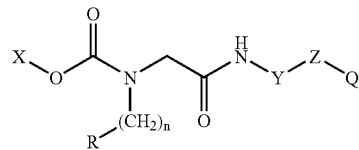

wherein X is a cytotoxic agent or therapeutic agent;

n is an integer from 0 to 6, wherein $(CH_2)_n$ is substituted or unsubstiuted, straight or branched chain, alkyl, alkenyl, alkynyl, cyclic, heterocyclic, aromatic, or heteroaromatic.

R is $N(R_1R_2)$, $OR_1$, or $SR_1$ where $R_1$ and $R_2$ are, independently, hydrogen or a lower alkyl group;

Y is an hydrophilic spacer sequence, or is omitted;

Z is a linking peptide, or is omitted; and

Q is a targeting moiety.

According to the present invention, the release rate of cytotoxic agent may be controlled by modifying the chemical structure of the conjugate. For example, when R is $NH_2$ and n=2, the following displacement reaction can occur:

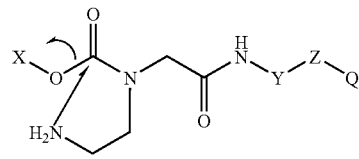

Without wishing to be bound by any theory, in the above mechanism, the nucleophilic group aids in the intracellular release of cytotoxic or therapeutic agent (as "X—OH") in an adjustable fashion dependent on n. The reactivity of the nucleophile may be increased or decreased according to the length of the hydrocarbon side chain, i.e., according to the value of n, or by changing R to $NCH_3$, OH, or $N(CH_3)_2$. For example, n=2 is preferable when the cytotoxic group is bound to the carbamate linkage through an alkyl-OH group, e.g., campotechin, homocamptothecin, colchicine, combretastatin, dolistatin, doxorubicin, methotrexate, podophyllotoxin, rhizoxin, rhizixin D, rocaglamide, anguidine, a taxol, pactlitoxol, CC1065, or a maytansinoid. However, when the cytotoxic group is bound through an aryl-OH group (e.g., combretastatin or rocaglamide) R is $N(CH_3)2$ and n=3 is preferable:

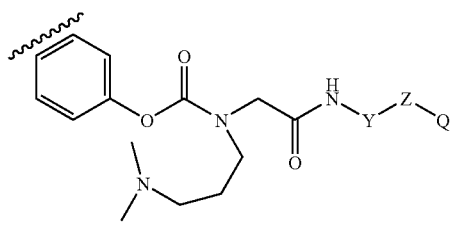

Thus, it is apparent from the teachings herein that conjugates of the invention may be designed to control the release of the cytotoxic or therapeutic agent.

The invention also features a compound having the formula:

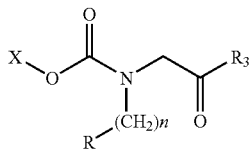

wherein

X is a cytotoxic agent or therapeutic agent;

n is an integer from 0 to 6, wherein $(CH_2)_n$ is substituted or unsubstituted, a straight or branched chain, or is an alkyl, alkenyl, alkynyl, cyclic, heterocyclic, aromatic, or heteroaromatic group;

R is $N(R_1R_2)$, $OR_1$, or $SR_1$ where $R_1$ and $R_2$ are, independently, hydrogen or a lower alkyl group, and wherein $R_3$ is a $(CH_2)SH$ group or an OH group. For example, a compound having the formula:

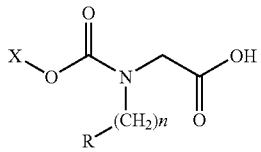

can be used to link the compound to a peptide, protein, or antibody. In addition, a peptide or protein can be directly synthesized onto this conjugate, thereby providing an easy means of preparing conjugate compounds containing a peptide or protein. The compound can be provided such that the R group is a tBoc protected primary or secondary amino group, and a peptide or protein can be added to the compound as described in the examples provided below.

Peptides, proteins, and antibodies can also be attached to a compound having the formula:

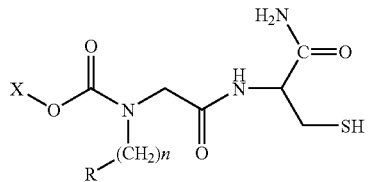

This unprotected R derivative can be used to link peptides, proteins, and antibodies using known thiol-reactive chemical reactions that attach to the thiol moiety at the $R_3$ position (see, e.g., Greg T. Hermanson, "Bioconjugate Techniques" p. 146-152, 1996, and EXAMPLE 21 below).

In all of the conjugates of the invention, X is preferably selected from cytotoxic agents and therapeutic agents containing a primary, secondary, tertiary, benzylic or phenolic hydroxyl group. One skilled in the art will recognize that, for those cytotoxic or therapeutic agents which lack a hydroxyl group, a derivative containing such a hydroxyl group may be prepared using procedures known in the art.

Preferred cytotoxic agents are those used for cancer therapy, such as, in general, alkylating agents, anti-proliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. As noted previously, one skilled in the art may make chemical modifications to the desired compound in order to make reactions of that compound more convenient for purposes of preparing conjugates of the invention. In preferred embodiments, X is a cytotoxic agent selected from camptothecin, homocamptothecin, colchicine, combretastatin, dolistatin, doxorubicin, methotrexate, podophyllotixin, rhizoxin, rhizoxin D, a taxol, paclitaxol, CC1065, or a maytansinoid, and derivatives and analogs thereof. For example, the cytotoxic agent camptothecin is linked through its single free hydroxyl group to a carbamate linker and thiocolchicine can be derivatized such that it contains a hydroxy group suitable for use of the described linking group strategy. In this embodiment of the invention, n is preferably 2 and R is preferably $NH_2$.

In conjugates of the present invention, X can be any cytotoxic or therapeutic moiety, e.g., Antineoplastic agents such as: Acivicin; Aclarubicin; Acodazole Hydrochloride; Acronine; Adozelesin; Adriamycin; Aldesleukin; Altretamine; Ambomycin; A. metantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium;Bropirimine; Busulfan; Cactinomycin; Calusterone; Camptothecin; Caracemide; Carbetimer; Carboplatin; Carmustine; Carubicin Hydrochloride; Carzelesin; Cedefingol; Chlorambucil; Cirolemycin; Cisplatin; Cladribine; Colchicine; Combretestatin A-4; Crisnatol Mesylate; Cyclophosphamide; Cytarabine; Dacarbazine;DACA (N-[2-(Dimethylamino)ethyl]acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Dolasatins; Doxorubicin; Doxorubicin Hydrochloride; Droloxifene; Droloxifene Citrate; Dromostanolone Propionate; Duazomycin; Edatrexate; Eflornithine Hydrochloride; Ellipticine; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Homocamptothecin; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin;

Mitomycin; Mitosper; Mitotane; Mitoxantrone Hydrochloride; Mycophenolic Acid; Nocodazole; Nogalamycin;Ormaplatin; Oxisuran; Paclitaxel; Pegaspargase; Peliomycin; Pentamustine; PeploycinSulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Rhizoxin; Rhizoxin D; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiocolchicine; Thiamiprine; Thioguanine; Thiotepa; Thymitaq; Tiazofurin; Tirapazamine; Tomudex; TOP53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine;Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2' Deoxyformycin; 9-aminocamptothecin; raltitrexed; N-propargyl-5,8-dideazafolic acid; 2chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N, N'-Bis (2-chloroethyl)-N-nitrosourea (BCNU); N-(2-chloroethyl)-N' cyclohexyl-N-nitrosourea (CCNU); N-(2-chloroethyl)-N'- (trans-4-methylcyclohexyl-Nnitrosourea (MeCCNU); N-(2-chloroethyl)-N'-(diethyl) ethylphosphonate-N-nitrosourea (fotemustine);streptozotocin; diacarbazine (DTIC); mitozolomide; temozolomide; thiotepa; mitomycin C; AZQ; adozelesin; Cisplatin; Carboplatin; Ormaplatin; Oxaliplatin;C1-973; DWA 2114R; JM216; JM335; Bis (platinum); tomudex; azacitidine; cytarabine; gemcitabine; 6-Mercaptopurine; 6-Thioguanine; Hypoxanthine; teniposide 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans apthal; 14-hydroxy-retro-retinol; all-trans retinoic acid; N-(4-Hydroxyphenyl)retinamide; 13-cis retinoic acid; 3-Methyl TTNEB; 9-cis retinoic acid; fludarabine (2-F-ara-AMP); or 2-chlorodeoxyadenosine (2-Cda).

Other suitable anti-neoplastic compounds include, but are not limited to, 20-pi-1,25 dihydroxyvitamin D3; 5-ethynyluracil; abiraterone; aclarubicin; acylfulvene; adecypenol; adozelesin; aldesleukin; all-tyrosine kinase antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; basic fibroblast growth factor (bFGF) inhibitor, bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e. g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer;

ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor, retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

X may also be an antiproliferative agent, for example piritrexim isothionate. Alternatively, X may be an antiprostatic hypertrophy agent such as, for example, sitogluside, a benign prostatic hyperplasia therapy agent such as, for example, tamsulosin hydrochloride, or a prostate growth inhibitor such as, for example, pentomone.

X can also be a radioactive agent, including, but not limited to: Fibrinogen $^{125}$I; Fludeoxyglucose $^{18}$F; Fluorodopa $^{18}$F; Insulin $^{125}$I; Insulin $^{131}$I; Iobenguane $^{123}$I; Iodipamide Sodium $^{131}$I; Iodoantipyrine $^{131}$I; Iodocholesterol $^{131}$I; Iodohippurate Sodium $^{123}$I; Iodohippurate Sodium $^{125}$I; Iodohippurate Sodium $^{131}$I; Iodopyracet $^{125}$I; Iodopyracet $^{131}$I; Iofetamine Hydrochloride $^{123}$I; Iomethin $^{125}$I; Iomethin $^{131}$I; Iothalamate Sodium $^{125}$I; Iothalamate Sodium $^{131}$I; tyrosine $^{131}$I; Liothyronine $^{125}$I; Liothyronine $^{131}$I; Merisoprol Acetate $^{197}$Hg; Merisoprol Acetate $^{203}$Hg; Merisoprol $^{197}$Hg; Selenomethionine $^{75}$Se; Technetium $^{99m}$Tc Antimony Trisulfide Colloid; Technetium $^{99m}$Tc Bicisate; Technetium $^{99m}$Tc Disofenin; Technetium $^{99m}$Tc Etidronate; Technetium $^{99m}$Tc Exametazime; Technetium $^{99m}$Tc Furifosmin; Technetium $^{99m}$Tc Gluceptate; Technetium $^{99m}$Tc Lidofenin; Technetium $^{99m}$Tc Mebrofenin; Technetium $^{99m}$Tc Medronate; Technetium $^{99m}$Tc Medronate Disodium; Technetium $^{99m}$Tc Mertiatide; Technetium $^{99m}$Tc Oxidronate; Technetium $^{99m}$Tc Pentetate; Technetium $^{99m}$Tc Pentetate Calcium Trisodium; Technetium $^{99m}$Tc Sestamibi; Technetium $^{99m}$Tc Siboroxime; Technetium $^{99m}$Tc; Succimer; Technetium $^{99m}$Tc Sulfur Colloid; Technetium $^{99m}$Tc Teboroxime; Technetium $^{99m}$Tc Tetrofosmin; Technetium $^{99m}$Tc Tiatide; Thyroxine $^{125}$I; Thyroxine $^{131}$I; Tolpovidone $^{131}$I; Triolein $^{125}$I; or Triolein $^{131}$I.

Other suitable therapeutic or cytotoxic agents used in conjugate of the invention include, for example, anti-cancer Supplementary Potentiating Agents, including, but not limited to: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); Ca++ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

The conjugates of the invention also can be administered with cytokines such as granulocyte colony stimulating factor. Preferred anticancer agents used in anti-cancer cocktails (e.g., in combination with the agents of the invention) include (some with their MTDs shown in parentheses): gemcitabine (1000 mg/m$^2$); methotrexate (15 gm/m$^2$ i.v.+leuco.<500 mg/m$^2$ i.v. w/o leuco); 5-FU (500 mg/m$^2$/day×5 days); FUDR (100 mg/kg×5 in mice, 0.6 mg/kg/day in human i.a.); FdUMP; Hydroxyurea (35 mg/kg/d in man); Docetaxel (60-100 mg/m$^2$); discodermolide; epothilones; vincristine (1.4 mg/m$^2$); vinblastine (escalating: 3.3-11.1 mg/m$^2$, or rarely to 18.5 mg/m$^2$); vinorelbine (30 mg/m$^2$/wk); meta-pac; irinotecan (50-150 mg/m$^2$, 1 x/wk depending on patient response); SN-38 (-100 times more potent than Irinotecan); 10-OH campto; topotecan (1.5 mg/m$^2$/day in humans, 1×iv LdlOmice=75 mg/m$^2$); etoposide (100 mg/m$^2$ in man); adriamycin; flavopiridol; Cis-Pt (100 mg/m$^2$ in man); carbo-Pt (360 mg/m$^2$ in man); bleomycin (20 mg/m2); mitomycin C (20 mg/m$^2$); mithramycin (30 sug/kg); capecitabine (2.5 g/m$^2$ orally); cytarabine (100 mg/m$^2$/day); 2-Cl-2'deoxyadenosine; Fludarabine-P04 (25 mg/m$^2$/day, ×5days); mitoxantrone (12-14 mg/m$^2$); mitozolomide (>400 mg/m$^2$); Pentostatin; and Tomudex.

X may preferably be an antimetabolic agent, such as methotrexate. Antimetabolites include, but are not limited to, the following compounds and their derivatives: azathioprine, cladribine, cytarabine, dacarbazine, fludarabine phosphate, fluorouracil, gencitabine chlorhydrate, mercaptopurine, methotrexate, mitobronitol, mitotane, proguanil chlorohydrate, pyrimethamine, raltitrexed, trimetrexate glucuronate, urethane, vinblastine sulfate, vincristine sulfate, etc. More preferably, X may be a folic acid-type antimetabolite, a class of agents that includes, for example, methotrexate, proguanil chlorhydrate, pyrimethanime, trimethoprime, or trimetrexate glucuronate, or derivatives of these compounds.

In another embodiment, X can also be a member of the anthracycline family of neoplastic agents, including but not limited to aclarubicine chlorhydrate, daunorubicine chlorhydrate, doxorubicine chlorhydrate, epirubicine chlorhydrate, idarubicine chlorhydrate, pirarubicine, or zorubicine chlorhydrate. Furthermore, X may be a camptothecin, or its derivatives or related compounds such as 10, 11 methylenedioxycamptothecin. X may also be selected from the maytansinoid family of compounds, which includes a variety of structurally related compounds. For example, ansamitocin P3, maytansine, 2'-N-demethylmaytanbutine, or maytanbicyclinol are maytansinoids.

Y is an hydrophilic spacer sequence that may be, preferably, a peptide that increases the biodistribution of the conjugate, or a hydrophilic polymer. For example, Y may be a peptide sequence that increases the hydrophilic biodistribution of the biologically active peptide conjugate. In a preferred embodiment, Y has the formula $U(V-V)_n$, wherein U is D-Pro, L-Pro, D-4-OH-Pro, L-4-OH-Pro, Sarcosine, Lys, Orn, Dab, Dap, 4-NH$_2$-Phe, or (NH$_2$—(CH$_2$)$_m$—COOH), where m=2-10, inclusive, or is deleted; each V is independently selected from the group consisting of: D-Ser, L-Ser, D-Thr, L-Thr, D-Gln, L-Gln, D-Asn, L-Asn, D-4-OH-Pro, or LA hydroxy-Pro; and n=1-50, inclusive. In another preferred embodiment, each V is independently D-Ser or L-Ser. In another preferred embodiment, at least one V is a D-amino acid.

Following the teachings herein, Y may be selected to facilitate biodistribution of a conjugate of the invention. Y may be a peptide or a polymer such as PEG or PVA. If Y is a hydrophilic peptide, Y may preferably be 1 to 50 amino acids in length, or more preferably 3 to 15 residues in length. For example, Y may be 3, 4, 5, 6, 7, 8, 9, 10, 11, 12, 13, 14, 15, 16, 17, 18, 19 or 20 amino acid residues in length. When a peptide, Y may contain charged or non-polar amino acids, their analogs or derivatives that are naturally occurring, synthetic or modified.

Y can also be a hydrophilic polymer. For example, Y may be polyethylene glycol (PEG), polyvinyl acetate, polyvinyl alcohol (PVA), N-2-hydroxypropyl) methacrylamide (HPMA) or HPMA copolymers, α,β-poly(N-hydroxyethyl)-DL-aspartamide (PHEA), or α,β-poly(N-hydroxypropyl)-DL-aspartamide. PEG, PHEA, and PVA groups used in conjugates of the invention are also known to be excellent promoters of rapid renal secretion which is correlated generally with lower potential drug toxicities (see, e.g., Yamoaka et al., J. Pharmacol. Sci., 83:601-606,1994; Rypacek et al., Pflugers Arch., 392:211-217, 1982; Yamoaka et al., J. Pharm. Pharmacol., 47:479-486, 1995). These groups may also promote lowered toxicity emanating from bioavailable, non-internalized conjugates.

Z is a linking peptide that preserves at least fifty percent of the biological activity of Q, when Z is bonded to Q through the terminal or side-chain amino group of Q. Generally, Z may be a peptide of 2, 3, 4, or 5 residues. Z has the formula: A-B-C-E-F, where A is D-Lys, D-Tyr, D-Ser, or L-Ser, or deleted; B is D-Lys or D-Tyr, or is deleted; C is Lys, Ser, hSer, Thr, Nle, Abu, Nva, (2,3, or 4) 3-pyridyl-Ala (Pal), Orn, Dab, Dap, 4-NH$_2$-Phe, D-4-OH-Pro, or L-4-OH-Pro, or is deleted; E is D-Lys, D-Tyr, D-Ser, D-4-OH-Pro, L-4-OH-Pro, 3-iodo-D-Tyr, 3-5 diido-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; and F is D-Lys, D-Tyr, D-Ser, L-Ser, D-4-OH-Pro, L-4-OH-Pro, 3-iodo-D-Tyr, 3-5 diido-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; provided that when A, B, C, and E are Tyr, Tyr, Lys, and Tyr, respectively, F is not Lys; and when A, B, C, and E, are Lys, Tyr, Lys, and Tyr, respectively, F is not Tyr or Lys; and when A and B are deleted, and C and E are Lys and Tyr, respectively, F is not Tyr or Lys.

In other embodiments, Z has the formula (when A, B, and C are deleted):

E-F where E is D-Lys, D-Tyr, D-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; and F is D-Lys, D-Tyr, D-Ser, L-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln.

In preferred embodiments, Z is D-Ser-Nle-D-Ser-D-Ser (SEQ ID NO: 1), D-Ser-Lys-D-Ser-D-Ser (SEQ ID NO: 2), D-Ser-Lys-D-Tyr-D-Tyr (SEQ ID NO: 3), D-Ser-Lys-D-Tyr-D-Ser (SEQ ID NO: 4), D-Ser-Ser-D-Lys-D-Ser (SEQ ID NO: 5), D-Ser-Ser-D-Lys-Ser (SEQ ID NO: 5), D-Ser-Nle-D-Tyr-D-Ser (SEQ ID NO: 6), D-Ser-Pal-D-Tyr-D-Ser (SEQ ID NO: 7), D-Ser-Thr-D-Tyr-D-Ser (SEQ ID NO: 8), Lys-D-Ser-D-Ser (SEQ ID NO: 9), Ser-D-Lys-D-Ser (SEQ ID NO: 10), Ser-D-Lys-Ser (SEQ ID NO: 10), Nle-D-Tyr-D-Ser (SEQ ID NO: 11), Lys-D-Tyr-D-Ser (SEQ ID NO: 12), Pal-D-Lys-D-Ser (SEQ ID NO: 13), Thr-D-Tyr-D-Ser (SEQ ID NO: 14), D-Ser-D-Lys, D-Ser-D-Tyr, D-Lys-D-Lys, D-Lys-D-Tyr, or D-Tyr-D-Lys.

Q is a targeting moiety, such as a biologically active peptide. Non-immunoreactive protein, polypeptide, or peptide ligands which can be used to form the conjugates of this invention include, but are not limited to, transferrin, epidermal growth factors ("EGF"), bombesin, gastrin, gastrin-releasing peptide, platelet-derived growth factor, IL-2, IL-6, tumor growth factors ("TGF"), such as TGF-α and TGF-β, vaccinia growth factor ("VGF"), insulin and insulin-like growth factors I and II. Non-peptidyl ligands may include, for example, steroids, carbohydrates, vitamins, and lectins.

In preferred embodiments, Q is a peptide, such as somatostatin, a somatostatin analog, bombesin, a bombesin analog, or an antibody, such as a monoclonal antibody. Preferred biologically active peptide or targeting moieties are internalized by select cells via an active internalization process, such as when binding to a G-Protein coupled receptor or somatostatin type 2 receptors (SSTR2).

The conjugates of the invention inhibit accumulation of toxic peptides in tissues through inclusion of the Z group (or linking peptide (i.e., peptide terminal extension)), containing hydrophilic residues, and optional inclusion of an hydrophilic spacer sequence. These components promote rapid elimination of intact, non-bound peptides through the kidneys.

The conjugates of the invention are designed to preserve full biological potency of the biologically-active peptides when conjugated to a cytotoxic agent. A peptide analog of the invention has a biological potency that is preferably greater than or equal to the parent peptide analog from which it is derived, with a specificity that is greater, lesser, or equivalent to the parent peptide's target specificity. For example, a somatostatin analog may bind to more somatostatin receptor subtypes than naturally-occurring somatostatin, or it may bind to a particular receptor subtype. Some analogs of the invention contain D-isomers of amino acids, or analogs thereof, facilitating stable coupling of cytotoxic agents while retaining high receptor affinity and biological potency of the peptide analog.

The cytotoxic or therapeutic conjugates of the invention can employ any of the large number of known somatostatin analogs that recognize the somatostatin receptor, such as those described above. Preferably, the somatostatin analog portion of the conjugate contains between 10 and 18 amino acids, and includes the core sequence: cyclo[Cys-Phe-D-Trp-Lys-Thr-Cys] (SEQ ID NO: 37 and SEQ ID NO: 38). Preferably, the C-terminus of the analog is: Thr-NH2. Bombesin analogs, as disclosed herein, may also be conjugated to cytotoxic or therapeutic agents in the peptide agents of the invention.

Specific targeting of therapeutic or cytotoxic agents allows selective destruction of a tumor expressing a receptor specific for a biologically active peptide. For example, a tumor expressing a somatostatin receptor includes a neoplasm of the lung, breast, prostate, colon, brain, gastrointestinal tract, neuroendocrine axis, liver, kidney, etc. (see Schaer et al., Int. J. Cancer, 70:530-537, 1997; Chave et al., Br. J. Cancer 82(1): 124-130, 2000; Evans et al., Br. J. Cancer 75(6):798-803, 1997).

Peptides for use in conjugates of the invention include KiSS peptides and analogs, urotensin II peptides and analogs, GnRH I and II peptides and analogs, octreotide, depreotide, vapreotide, vasoactive intestinal peptide (VIP), cholecystokinin (CCK), insulinlike growth factor (IGF), RGD-containing peptides, melanocyte-stimulating hormone (MSH) peptide, neurotensin, calcitonin, peptides from complementarity determining regions of an antitumor antibody, glutathione, YIGSR (leukocyte-avid peptides, e.g., P483H, which contains the heparin-binding region of platelet factor-4 (PF-4) and a lysine-rich sequence), atrial natriuretic peptide (ANP), β-amyloid peptides, delta-opioid antagonists (such as ITIPP (psi)), annexin-V, endothelin, IL-1, IL-1ra, IL-2, IL-8, leukotriene B4 (LTB4), chemotactic peptides (e.g., N-formyl-methionyl-leucyl-phenylalanine-lysine (fMLFK)), GP Iib/IIIa receptor antagonists (e.g., DMP444), epidermal growth factor, human neutrophil elastase inhibitor (EPI-HNE-2 and EPI-HNE-4), plasmin inhibitor, antimicrobial peptides, apticide (P280 and P274), thrombospondin receptor (including analogs such as TP-1300), bitistatin, pituitary adenylyl cyclase type I receptor (PAC1), fibrin α-chain, peptides derived from phage display libraries, and conservative substitutions thereof, that are targeted to a cell or tissue in the body of a mammal (e.g., diseased tissue, such as a tumor or a proliferative angiogenic blood vessel; see, e.g., those described by Aina et al., Biopolymers 66:184-199, 2002), and derivatives and analogs thereof. See, e.g., Signore et al., Eur. J. Nucl. Med. 28(10):1555-65, 2001.

Cytotoxic somatostatin peptide analogs may also be specific for tumor vasculatures, or angiogenic blood vessels, such as those which over-express somatostatin receptors (see Denzler and Reubi, Cancer 85:188-198, 1999; Gulec et al., J. Surg. Res. 97(2):131-137, 2001; Woltering et al., J. Surg. Res. 50:245, 1991). Additionally, because the preferred somatostatin analogs of the invention are variously hydrophilic, they are water-soluble and, thus, have enhanced use as compared to previous hydrophobic analogs. The hydrophilic analogs described herein are soluble in blood, cerebrospinal fluid, and other bodily fluids, as well as in urine, facilitating excretion by the kidneys. This hydrophilic character facilitates the delivery of the analogs of the invention to almost every area of the body. The invention also discloses specific hydrophilic elements for incorporation into peptide analogs, allowing modulation of the analog's hydrophilicity to adjust for the chemical and structural nature of the various conjugated cytotoxic agents.

Somatostatin agonist analogs are rapidly internalized after binding to their receptors (see, e.g., Lukinius et al, Acta Onc., 38:383-387, 1999) and can thus be used as vectors for targeting various therapeutic agents—such as traditional tumor cytotoxic agents. It is possible that the specificity of such anti-tumor agents can be drastically improved since many tumor types heavily overexpress somatostatin type 2 receptors. In this manner, we propose that the toxic side effects associated with all conjugatable cytotoxic agents can be usefully lowered as long as a potent hybrid molecule can be designed which retains very high affinity for somatostatin receptors.

Immunoreactive ligands for use as a targeting moiety in the invention include an antigen-recognizing immunoglobulin (also referred to as "antibody"), or antigen-recognizing fragment thereof. Particularly preferred immunoglobulins are those that can recognize a tumor-associated antigen. As used herein, "immunoglobulin" refers to any recognized class or subclass of immunoglobulins such as IgG, IgA, IgM, IgD, or IgE. Preferred are those immunoglobulins which fall within the IgG class of immunoglobulins. The immunoglobulin can be derived from any species. Preferably, however, the immunoglobulin is of human, murine, or rabbit origin. In addition, the immunoglobulin may be polyclonal or monoclonal, but is preferably monoclonal.

Conjugates of the invention may include an antigen-recognizing immunoglobulin fragment. Such immunoglobulin fragments may include, for example, the Fab', F(ab')$_2$, F$_v$, or Fab fragments, or other antigen-recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See Parham, J. Immunology, 131, 2895, 1983; Lamoyi et al., J. Immunological Methods, 56, 235, 1983.

The immunoglobulin used in conjugates of the invention may be a "chimeric antibody" as that term is recognized in the art. Also, the immunoglobulin may be a "bifunctional" or "hybrid" antibody, that is, an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. Hybrid antibodies thus have a dual specificity, preferably with one or more binding sites specific for the hapten of choice or one or more binding sites specific for a target antigen, for example, an antigen associated with a tumor, an infectious organism, or other disease state.

Biological bifunctional antibodies are described, for example, in European Patent Publication, EPA 0 105 360, which is hereby incorporated by reference in its entirety. Such hybrid or bifunctional antibodies may be derived either biologically, by cell fusion techniques, or chemically, such as with cross-linking agents or disulfide bridge-forming reagents, and may be comprised of whole antibodies and/or fragments thereof. Methods for obtaining such hybrid antibodies are disclosed, for example, in PCT application W083/03679, published Oct. 27, 1983, and published European Application EPA 0 217 577, published Apr. 8, 1987, each of which is hereby incorporated by reference in its entirety. Particularly preferred bifunctional antibodies are those biologically prepared from a "polydoma" or "quadroma" or which are synthetically prepared with cross-linking agents such as bis-(maleimido)-methyl ether ("BMME"), or with other cross-linking agents familiar to those skilled in the art In addition, the immunoglobin may be a single chain antibody ("SCA"). An SCA may consist of single chain Fv fragments ("scFv") in which the variable light ("$V_L$") and variable heavy ("$V_H$") domains are linked by a peptide bridge or by disulfide bonds. Also, the immunoglobulin may consist of single $V_H$ domains (dabs) that possess antigen-binding activity. See G. Winter and C. Milstein, Nature 349:295,1991; R. Glockshuber et al., Biochemistry 29:1362, 1990; and, E. S. Ward et al., Nature 341:544, 1989.

Especially preferred for use in the present invention are chimeric monoclonal antibodies; preferably those chimeric antibodies having specificity toward a tumor associated antigen. As used herein, the term "chimeric antibody" refers to a monoclonal antibody comprising a variable region, i.e. a binding region, from one source or species and at least a portion of a constant region derived from a different source or species, usually prepared by recombinant DNA techniques. Chimeric antibodies having a murine variable region and a human constant region are especially preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies for use in conjugates of the invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See Morrison, S. L, et al., Proc. Nat'l Acad. Sci., 81:6851, 1984.

The term "chimeric antibody" also includes a "humanized antibody," namely, those antibodies in which the framework or "complementarity determining regions" ("CDR") have been modified to include the CDR of an immunoglobulin of different specificity, as compared to that of the parent immunoglobulin. In a preferred embodiment, a murine CDR is grafted into the framework region of a human antibody to prepare the "humanized antibody." See, e.g., L. Riechmann et al., Nature 332:323, 1988; M. S. Neuberger et al., Nature 314:268, 1985. Particularly preferred CDRs correspond to those representing sequences recognizing the antigens noted above for the chimeric and bifunctional antibodies. See, e.g., EPA 0 239 400 (published Sep. 30, 1987), which is hereby incorporated by reference in its entirety.

One skilled in the art will recognize that a bifunctional-chimeric antibody can be prepared which would have the benefits of lower immunogenicity of the chimeric or humanized antibody, as well as the flexibility, especially for therapeutic treatment, of the bifunctional antibodies described above. Such bifunctional-chimeric antibodies can be synthesized, for instance, by chemical synthesis using cross-linking agents and/or recombinant methods of the type described above. The present invention should not be construed as limited in scope by any particular method of production of an antibody whether bifunctional, chimeric, bifunctional-chimeric, humanized, or an antigen-recognizing fragment or derivative thereof.

Conjugates of the invention may also include immunoglobulins (as defined above) or immunoglobulin fragments to which are fused active proteins, for example, an enzyme of the type disclosed in Neuberger, et al., PCT application WO86/01533, published Mar. 13, 1986, which is hereby incorporated by reference in its entirety.

As used herein, "bifunctional," "fused," "chimeric" (including humanized), and "bifunctional-chimeric" (including humanized) antibody constructions also include, within their individual contexts, constructions including antigen recognizing fragments. As one skilled in the art will recognize, such fragments may be prepared by traditional enzymatic cleavage of intact bifunctional, chimeric, humanized, or chimeric-bifunctional antibodies. In the event that intact antibodies are not susceptible to such cleavage, e.g., because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin "fragment." It is in this context that the term "fragment" is used herein.

The immunoglobulin (antibody), or fragment thereof, used in conjugates of the present invention may be polyclonal or monoclonal in nature. Monoclonal antibodies are the preferred immunoglobulins. The preparation of polyclonal or monoclonal antibodies is well known to those skilled in the art. See, e.g., G. Kohler and C. Milstein, Nature 256:495, 1975. In addition, hybridomas and/or monoclonal antibodies which are produced by such hybridomas and which are useful in the practice of the present invention are publicly available.

In a further embodiment, the invention features a method for the treatment of a disease or modification of a biological function. The method includes administering to a warm-blooded animal in need thereof, a therapeutically effective or biological function modifying amount of a conjugate of the invention. One of skill in the art will recognize that the particular conjugate used will depend on the disease state to be treated or the biological system to be modified. In particular, one skilled in the art will be able to select a particular targeting moiety and cytotoxic or therapeutic agent to prepare a conjugate of the invention which has specificity for the treatment of the disease or is able to modify the biological function desired. It is envisioned that several disease are treatable using the conjugates of the invention, including, for example, tumors of the lung, breast, brain, eye, prostate or colon; tumors of neuroendocrine origin (e.g., carcinoid syndrome); and proliferative angiogenic blood vessels (in, e.g., the eye), such as those associated with tumors, retinal macular degeneration, or diabetic retinopathy.

Conjugates of the invention may be administered to a mammalian subject, such as a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in Remington's Pharmaceutical Sciences, (18$^{th}$ edition), ed. A. Gennaro, 1990, Mack Publishing Company, Easton, Pa.

Pharmaceutical formulations of a therapeutically effective amount of a conjugate of the invention, or pharmaceutically acceptable salt-thereof, can be administered orally, parenterally (e.g., intramuscular, intraperitoneal, intravenous, subcutaneous, or ocular injection, inhalation, intradermally, optical drops, or implant), nasally, vaginally, rectally, sublingually or topically, in admixture with a pharmaceutically acceptable carrier adapted for the route of administration.

Methods well known in the art for making formulations are found, for example, in Remington's Pharmaceutical Sciences (18$^{th}$ edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the polypeptides of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, formulations can also be manufactured in the form of sterile, solid compositions that can be dissolved in sterile water or some other sterile injectable medium immediately before use.

Compositions for rectal or vaginal administration are preferably suppositories that may contain, in addition to active substances, excipients such as cocoa butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient in the compositions of the invention can be varied. One skilled in the art will appreciate that the exact individual dosages may be adjusted somewhat depending upon a variety of factors, including the polypeptide being administered, the time of administration, the route of administration, the nature of the formulation, the rate of excretion, the nature of the subject's conditions, and the age, weight, health, and gender of the patient In addition, the severity of the condition targeted by the biologically active peptide such as somatostatin or bombesin will also have an impact on the dosage level. Generally, dosage levels of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The conjugates of the invention can be administered in a sustained release composition, such as those described in, for example, U.S. Pat. No. 5,672,659 and U.S. Pat. No. 5,595,760. The use of immediate or sustained release compositions depends on the type of condition being treated. If the condition consists of an acute or over-acute disorder, a treatment with an immediate release form will be preferred over a prolonged release composition. Alternatively, for preventative or long-term treatments, a sustained released composition will generally be preferred.

Polypeptides used in the present invention can be prepared in any suitable manner. The polypeptides may be isolated from naturally occurring sources, recombinantly produced, or produced synthetically, or produced by a combination of these methods. The synthesis of short peptides is well known in the art. See e.g. Stewart et al., Solid Phase Peptide Synthesis (Pierce Chemical Co., 2d ed., 1984). The peptides of the present invention can be synthesized according to standard peptide synthesis methods known in the art.

The following examples are meant to illustrate the invention. They are not meant to limit the invention in any way.

EXAMPLE 1

Preparation of the chloroformate of camptothecin

Camptothecin (250 mg) and 4-dimethylaminopyridine (DMAP; 50 mg) were suspended in 3 mL anhydrous pyridine and 50 mL anhydrous methylene chloride. Phosgene (750 µL of a 20% solution in toluene) was added to the slurry and mixed 2 h at ambient temperature. Excess phosgene and methylene chloride were evaporated in a chemical fume hood and the chlorformate of camptothecin dissolved in DCM.

EXAMPLE 2

Preparation of Camptothecin-carbonyl-N-aminoethyl-glycine-D-tert-butyl-Ser-Nle-D-tert-butyl-Tyr-D-tert-butyl-Ser-S-trityl-Cys-Phe-D-Trp-epsilon-tert-butyloxycarbonyl-Lys-tert-butyl-Thr-S-trityl-Cys-tert-butyl-Thr-Rink-amide-resin (SEQ ID NO: 16)

Rink amide [4-(2',4'-dimethoxyphenyl-Fmoc-(aminomethyl)phenoxyacetamido-norleucyl-methylbenzhydrylamine resin (0.063 mmole), 100-200 mesh (Novabiochem, San Diego, Calif.) was added to the reaction vessel of a CS136 automatic peptide synthesizer (CS Bio, Inc., San Carlos, Calif.) and swollen in dimethylformamide (DMF) for approximately 1 hour. The resin was filtered and an excess of 20% piperidine in DMP was added and mixed (2 min). The resin was filtered and again an excess amount of 20% piperidine added and mixed (20 min) to ensure complete removal of the resin Fmoc group. After deprotection, the resin was washed 4 times with DMF and then the first protected amino acid, Fmoc-Thr(tBut) (0.188 mmol), diisopropylcarbodiimide (DIC) (0.188 mmol), and N-hydroxybenzotriazole monohydrate (HOBt) (0.188 mmol) were all dissolved in DMF and added to the resin, which was mixed for 1 h, followed by washing 4 times with DMF.

The Fmoc group was again removed by treatment with 20% piperidine/DMF solution and, following the same general coupling procedures, the following amino acids were successively reacted with the growing peptide chain: Fmoc-S-trityl-L-cysteine, Fmoc-O-t-butyl-L-threonine, $N^\alpha$-Fmoc-$N^\epsilon$-Boc-L-lysine, $N^\alpha$-Fmoc-$N^{in}$-Boc-D-tryptophan, Fmoc-L-phenylalanine, Fmoc-S-trityl-L-cysteine, Fmoc-O-t-butyl-D-serine, Fmoc-O-t-butyl-D-tyrosine, $N^\alpha$-Fmoc-Norleucine, Fmoc-O-t-butyl-D-serine, bromoacetic acid. After completion of bromoacetic acid coupling to peptidyl resin (3 eq), N-Boc-ethylenediamine was added in N-methyl-α-pyrrolidinone (NMP) and mixed (2 h) and then washed 3 times with DMF and 3 times with DCM. Camptothecin chloroformate from EXAMPLE 1 was added to the resin and mixed overnight, washed with copious amounts of DMF followed by methanol. After a final filtration the derivatized resin was air dried overnight.

EXAMPLE 3

Preparation of camptothecin-carbonyl-N-(2-aminoethyl)-glycine-D-Ser-Nle-D-Tyr-D-Ser-cyclo[Cys-Phe-D-Trp-Lys-Thr-Cys]-Thr-amide (SEQ ID NO: 17)

The camptothecin-peptide resin prepared in EXAMPLE 2 (0.063 mmol) was placed in a round bottomed flask to which was added 15 mL of a solution of trifluoroacetic acid (TFA) containing water (2.5%), 1,2-ethanedithiol (2.5%), and triisopropylsilane (1%). The suspension was agitated (2 h) and filtered and washed several times with TFA. The TFA was evaporated in vacuo and ether added to the resulting oil to give a yellow powder that was then dissolved in 60% acetic acid (250 mL). A concentrated solution of iodine in methanol was added dropwise with vigorous stirring until a permanent brown coloration was formed whereupon excess iodine was removed by addition of a small quantity of ascorbic acid.

The solution was reduced to a volume of around 10 mL in vacuo and the crude camptothecin peptide purified by preparative reverse phase high pressure liquid chromatography (RP-HPLC) on a column (21.4×250 mm) of C-18 bonded silica (Dynamax 300, 8 μm). A linear gradient elution system at a flow rat of 20 mL/min was employed: buffer A consisted of 0.1% TFA and buffer B, 0.1% TFA in 80% MeCN; 20% B to 50% B was increased at 1% per min. The separation was monitored at 280 nm. The fractions containing the pure product, as identified by analytical HPLC, were pooled, concentrated in vacuo, and subjected to lyophilization. The peptide was obtained as a fluffy yellow powder of constant weight by lyophilization from aqueous acetic acid. Correct composition was demonstrated by amino acid analysis of an acid hydrolysate and matrix assisted laser desorption mass spectrometry.

EXAMPLE 4

Preparation of chloroformate of paclitaxel

Paclitaxel (0.6 mmole) was dissolved in 30 mL anhydrous DCM in a 100 mL round bottomed (RB) flask. To this solution, diisopropylethylamine (DIEA; 3 mmol) dissolved in 20 mL anhydrous DCM was added over 20 minutes at 0° C. under a dry nitrogen atmosphere. Phosgene (3 mmol) was added to the slurry and mixed for 30 minutes at 0° C. and 2 hours at ambient temperature. Excess phosgene and methylene chloride were evaporated and the chloroformate of paclitaxel was dissolved in methylene chloride.

EXAMPLE 5

Preparation of Paclitaxel-carbonyl-N-(2-hydroxyethyl)-glycine-D-trityl-Ser-Norleucine-D-trityl-Tyr-D-trityl-Ser-S-trityl-Cys-Phe-D-Trp-epsilon-mtt-Lys-trityl-Thr-S-trityl-Cys-trityl-Thr-Amino-xanthen-MBHA-resin (SEQ ID NO: 16)

FMOC-Amino-Xanthen-MBHA (4-Methylbenzhydrylamine Hydrochloride) polystyrene resin (0.063 mmol) [Bachem, catalog # D-2040, Lot # 0541173] was added to the reaction vessel of a CS136 automatic peptide synthesizer (CS Bio, Inc., San Carlos, Calif.) and swollen in DMF for approximately 1 hour. The resin was filtered and an excess of 20% piperidine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Thr(trityl) (0.188 mmol), diisopropylcarbodiimide (DIC) (0.188 mmol), and N-hydroxybenzotriazole monohydrate (HOBt) (0.188 mmol) were all dissolved in DMF and added to the resin which was mixed (1 h) followed by washing 4 times with DMF.

The Fmoc group was again removed by treatment with 20% piperidine/DMF solution and, following the same general coupling procedures, the following amino acids were successively reacted with the growing peptide chain: Fmoc-S-trityl-L-cysteine, Fmoc-O-trityl-L-threonine, $N^\alpha$-Fmoc-$N^\epsilon$mtt-L-lysine, $N^\alpha$-Fmoc-D-tryptophan, Fmoc-L-phenylalanine, Fmoc-S-trityl-L-cysteine, Fmoc-O-trityl-D-serine, Fmoc-O-trityl-D-tyrosine, N-Fmoc-Norleucine, Fmoc-O-trityl-D-serine, Bromoacetic acid. After completion of bromoacetic acid coupling to peptidyl resin, (3 eq) ethanolamine was added in NMP and mixed for two hours then washed 3 times with DMF and 3 times with DCM. Paclitaxel chloroformate from EXAMPLE 4 was added to the resin and mixed overnight, washed with copious amounts of DMF followed by methanol. After a final filtration the derivatized resin was air dried overnight.

EXAMPLE 6

Preparation of Paclitaxel-carbonyl-N-(2-hydroxyethyl)-glycine-D-Ser-Me-D-Tyr-D-Ser-cyclo[Cys-Phe-D-Trp-Lys-Thr-Cys]-Thr-amide (SEQ ID NO: 17)

The paclitaxel-peptide resin prepared in EXAMPLE 5 (0.063 mmol) was placed in a RB flask to which was added 15 mL of a solution of trifluoroacetic acid (2%) in methylene chloride. The suspension was agitated (2 h), filtered, and washed several times with methylene chloride. The methylene chloride was evaporated in vacuo and ether added to the resulting oil to give a white powder that was then dissolved in 60% acetic acid (250 mL). A concentrated solution of iodine in methanol was added dropwise with vigorous stirring until a permanent brown coloration was formed whereupon excess iodine was removed by addition of a small quantity of ascorbic acid.

The solution was reduced to a volume of around 10 mL in vacuo and the crude paclitaxel peptide purified by preparative reverse phase high pressure liquid chromatography (RP-HPLC) on a column (21.4×250 mm) of C-18 bonded silica (Dynamax 300, 8 μm). A linear gradient elution system at a flow rat of 20 mL/min was employed: buffer A consisted of 0.1% TFA and buffer B, 0.1% TFA in 80% MeCN; 20% B to 50% B was increased at 1% per min. The separation was monitored at 280 mu. The fractions containing the pure product as evidenced by analytical HPLC were pooled, concentrated in vacuo, and subjected to lyophilization. The peptide was obtained as a fluffy white powder of constant weight by lyophilization from aqueous acetic acid. Correct composition was demonstrated by amino acid analysis of an acid hydrolysate and matrix assisted laser desorption mass spectrometry.

EXAMPLE 7

Preparation of Camptothecin-carbonyl-N-aminoethyl-glycine-D-tert-butyl-Ser-D-epsilon-tert-butyloxycarbonyl-Lys-Gln-Trp-Ala-Val-β-Ala-trityl-His-Phe-Nle-Rink-amide-resin (SEQ ID NO: 18)

Rink amide MBHA polystyrene resin (0.063 mmol) [4-(2', 4'-dimethoxyphenyl-Fmoc-(aminomethyl)phenoxyacetamido-norleucyl-methylbenzhydrylamine resin, 100-200 mesh, Novabiochem, San Diego, Calif.] was added to the reaction vessel of a CS136 automatic peptide synthesizer (CS Bio, Inc., San Carlos, Calif.) and swollen in DMF for approximately 1 hour. The resin was filtered and an excess of 20% piperidine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Norleucine) (0.188 mmol), diisopropylcarbodiimide (DIC) (0.188 mmol), and N-hydroxybenzotriazole monohydrate (HOBt) (0.188 mmol) were all dissolved in DMF and added to the resin which was mixed (1 h) followed by washing 4 times with DMF.

The Fmoc group was again removed by treatment with 20% piperidine/DMF solution and, following the same general coupling procedures, the following amino acids were successively reacted with the growing peptide chain: Fmoc-L-phenylalanine, Fmoc-$N^{im}$-trityl-L-histidine, Fmoc-βAla, Fmoc-Valine, Fmoc-alanine, Fmoc-$N^{in}$-Boc-L-tryptophan, Fmoc-glutamine, Fmoc-$N^g$-Boc-D-lysine, Fmoc-O-t-butyl-D-serine, bromoacetic acid. After completion of bromoacetic acid coupling to peptidyl resin, (3 eq) N-Boc-ethylenediamine was added in NMP and mixed for two hours then washed 3 times with DMF and 3 times with DCM. Camptothecin chloroformate from EXAMPLE 1 was added to the resin and mixed overnight, washed with copious amounts of DMF followed by methanol. After a final filtration the derivatized resin was air dried overnight.

EXAMPLE 8

Preparation of Camptothecin-carbonyl-N-(2-aminoethyl)-glycine-D-Ser-D-Lys-Gln-Trp-Ala-Val-β-Ala-His-Phe-Me-amide (SEQ ID NO: 18)

The camptothecin-peptide resin prepared in EXAMPLE 7 (0.063 mmol) was placed in a round bottomed flask to which was added 15 mL of a solution of trifluoroacetic acid (TFA) containing water (2.5%), and triisopropylsilane (1%). The suspension was agitated (2 h), filtered, and washed several times with TFA. The TFA was evaporated in vacuo and ether added to the resulting oil to give a yellow powder that was then dissolved in 60% acetic acid (250 mL).

The solution was reduced to a volume of around 10 mL in vacuo and the crude camptothecin peptide purified by preparative reverse phase high pressure liquid chromatography (RP-HPLC) on a column (21.4×250 mm) of C-18 bonded silica (Dynamax 300, 8 μm). A linear gradient elution system at a flow rat of 20 mL/min was employed: buffer A consisted of 0.1% TFA and buffer B, 0.1% TFA in 80% MeCN; 20% B to 50% B was increased at 1% per min. The separation was monitored at 280 nm. The fractions containing the pure product as evidenced by analytical HPLC were pooled, concentrated in vacuo, and subjected to lyophilization. The peptide was obtained as a fluffy yellow powder of constant weight by lyophilization from aqueous acetic acid. Correct composition was demonstrated by amino acid analysis of an acid hydrolysate and matrix assisted laser desorption mass spectrometry.

EXAMPLE 9

Preparation of Camptothecin-carbonyl-N-aminoethyl-glycine-D-tert-butyl-Ser-D-tert-butyl-Tyr-Gln-Trp-Ala-Val-β-Ala-trityl-His-Phe-Nle-Rink-amide-resin (SEQ ID NO: 19)

Rink amide MBHA polystyrene resin (0.063 mmol) [4-(2', 4'-dimethoxyphenyl-Fmoc-(aminomethyl)phenoxyacetamido-norleucyl-methylbenzhydrylamine resin, 100-200 mesh, Novabiochem, San Diego, Calif.] was added to the reaction vessel of a CS136 automatic peptide synthesizer (CS Bio, Inc., San Carlos, Calif.) and swollen in DMF for approximately 1 hour. The resin was filtered and an excess of 20% piperidine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Norleucine (0.188 mmol), diisopropylcarbodiimide (DIC) (0.188 mmol), and N-hydroxybenzotriazole monohydrate (HOBt) (0.188 mmol) were all dissolved in DMF and added to the resin which was mixed (1 h) followed by washing 4 times with DMF.

The Fmoc group was again removed by treatment with 20% piperidine/DMF solution and, following the same general coupling procedures, the following amino acids were successively reacted with the growing peptide chain: Fmoc-L-phenylalanine, Fmoc-$N^{im}$-trityl-L-histidine, Fmoc-βAla, Fmoc-Valine, Fmoc-alanine, Fmoc-$N^{in}$-Boc-L-tryptophan, Fmoc-glutamine, Fmoc-O-t-butyl-D-Tyr, Fmoc-O-t-butyl-D-serine, bromoacetic acid. After completion of bromoacetic acid coupling to peptidyl resin, (3 eq) N-Boc-ethylenediamine was added in NMP and mixed for two hours then washed 3 times with DMF and 3 times with DCM. Camptothecin chloroformate from EXAMPLE 1 was added to the resin and mixed overnight, washed with copious amounts of DMF followed by methanol. After a final filtration the derivatized resin was air dried overnight.

EXAMPLE 10

Preparation of Camptothecin-carbonyl-N-(2-aminoethyl)-glycine-D-Ser-D-Tyr-Gln-Trp-Ala-Val-β-Ala-His-Phe-Nle-amide (SEQ D NO: 19)

The camptothecin-peptide resin prepared in EXAMPLE 9 (0.063 mmol) was placed in a RB flask to which was added 15 mL of a solution of trifluoroacetic acid (TFA) containing water (2.5%), and triisopropylsilane (1%). The suspension was agitated (2 h), filtered and washed several times with TFA. The TFA was evaporated in vacuo and ether added to the resulting oil to give a yellow powder that was then dissolved in 60% acetic acid (250 mL).

The solution was reduced to a volume of around 10 mL in vacuo and the crude camptothecin peptide purified by preparative reverse phase high pressure liquid chromatography (RP-HPLC) on a column (21.4×250 mm) of C-18 bonded silica (Dynamax 300, 8 μm). A linear gradient elution system at a flow rat of 20 mL/min was employed: buffer A consisted of 0.1% TFA and buffer B, 0.1% TFA in 80% MeCN; 20% B to 50% B was increased at 1% per min. The separation was monitored at 280 run. The fractions containing the pure product as evidenced by analytical HPLC were pooled, concentrated in vacuo, and subjected to lyophilization. The peptide was obtained as a fluffy yellow powder of constant weight by lyophilization from aqueous acetic acid. Correct composition was demonstrated by amino acid analysis of an acid hydrolysate and matrix assisted laser desorption mass spectrometry.

EXAMPLE 11

Preparation of Combretastatin-carbonyl-N-(2-aminoethyl)-glycine-D-tert-butyl-Ser-Norleucine-D-tert-butyl-Tyr-D-tert-butyl-Ser-S-trityl-Cys-Phe-D-Trp-epsilon-tert-butyloxycarbonyl-Lys-tert-butyl-Thr-S-trityl-Cys-tert-butyl-Thr-Rink-amide-resin (SEQ ID NO: 39)

Rink amide MBHA polystyrene resin (0.063 mmole) [4-(2',4'-dimethoxyphenyl-Fmoc-(aminomethyl)phenoxyacetamido-norleucyl-methylbenzhydrylamine resin, 100-200 mesh, Novabiochem, San Diego, Calif.] was added to the reaction vessel of a CS136 automatic peptide synthesizer (CS Bio, Inc., San Carlos, Calif.) and swollen in DMF for approximately 1 hour. The resin was filtered and an excess of 20% piperidine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Thr(tBut) (0.188 mmol), diisopropylcarbodiimide (DIC) (0.188 mmol), and N-hydroxybenzotriazole monohydrate (HOBt) (0.188 mmol) were all dissolved in DMF and added to the resin which was mixed (1 h) followed by washing 4 times with DMF.

The Fmoc group was again removed by treatment with 20% piperidine/DMF solution and, following the same general coupling procedures, the following amino acids were successively reacted with the growing peptide chain: Fmoc-S-trityl-L-cysteine, Fmoc-O-t-butyl-L-threonine, $N^\alpha$-Fmoc-N-Boc-L-lysine, $N^\alpha$-Fmoc-$N^{in}$-Boc-D-tryptophan, Fmoc-L-phenylalanine, Fmoc-S-trityl-L-cysteine, Fmoc-O-t-butyl-D-serine, Fmoc-O-t-butyl-D-tyrosine, $N^\alpha$-Fmoc-Norleucine, Fmoc-O-t-butyl-D-serine, Bromoacetic acid. After completion of bromoacetic acid coupling to peptidyl resin, (3 eq) N-Boc-ethylenediamine was added in NMP and mixed for two hours then washed 3 times with DMF and 3 times with DCM. Combretastatin chloroformate from EXAMPLE 1 was added to the resin and mixed overnight, washed with copious amounts of DMF followed by methanol. After a final filtration the derivatized resin was air dried overnight

EXAMPLE 12

Preparation of combretastatin-carbonyl-N-(2-aminoethyl)-glycine-D-Ser-Me-D-Tyr-D-Ser-cyclo[Cys-Phe-D-Trp-Lys-Thr-Cys]-Thr-amide (SEQ ID NO: 40)

The combretastatin-peptide resin prepared in Example 11 (0.063 mmol) was placed in a round bottomed flask to which was added 15 mL of a solution of trifluoroacetic acid (TFA) containing water (2.5%), 1,2-ethanedithiol (2.5%), and triisopropylsilane (1%). The suspension was agitated (2 h), filtered and washed several times with TFA. The TFA was evaporated in vacuo and ether added to the resulting oil to give a white powder that was then dissolved in 60% acetic acid (250 mL). A concentrated solution of iodine in methanol was added dropwise with vigorous stirring until a permanent brown coloration was formed whereupon excess iodine was removed by addition of a small quantity of ascorbic acid.

The solution was reduced to a volume of around 10 mL in vacuo and the crude camptothecin peptide purified by preparative reverse phase high pressure liquid chromatography (RP-HPLC) on a column (21.4×250 mm) of C-18 bonded silica (Dynamax 300, 8 μm). A linear gradient elution system at a flow rat of 20 mL/min was employed: buffer A consisted of 0.1% TFA and buffer B, 0.1% TFA in 80% MeCN; 20% B to 50% B was increased at 1% per min. The separation was monitored at 280 nm. The fractions containing the pure product as evidenced by analytical HPLC were pooled, concentrated in vacuo and subjected to lyophilization. The peptide was obtained as a fluffy white powder of constant weight by lyophilization from aqueous acetic acid. Correct composition was demonstrated by amino acid analysis of an acid hydrolysate and matrix assisted laser desorption mass spectrometry.

EXAMPLE 13

Preparation of Camptothecin-carbonyl-N-(N-methyl-2-aminoethyl)-glycine-D-tert-butyl-Ser-Norleucine-D-tert-butyl-Tyr-D-tert-butyl-Ser-S-trityl-Cys-Phe-D-Trp-epsilon-tert-butyloxycarbonyl-Lys-tert-butyl-Thr-S-trityl-Cys-tert-butyl-Thr-rink-amide-resin (SEQ ID NO: 39)

Rink amide MBHA polystyrene resin (0.063 mmol) [4-(2', 4'-dimethoxyphenyl-Fmoc-(aminomethyl)phenoxyacetamido-norleucyl-methylbenzhydrylamine resin, 100-200 mesh, Novabiochem, San Diego, Calif.] was added to the reaction vessel of a CS136 automatic peptide synthesizer (CS Bio, Inc., San Carlos, Calif.) and swollen in DMF for approximately 1 hour. The resin was filtered and an excess of 20% piperidine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Thr(tBut) (0.188 mmol), diisopropylcarbodiimide (DIC) (0.188 mmol), and N-hydroxybenzotriazole monohydrate (HOBt) (0.188 mmol) were all dissolved in DMF and added to the resin which was mixed (1 h) followed by washing 4 times with DMF.

The Fmoc group was again removed by treatment with 20% piperidine/DMF solution and, following the same general coupling procedures, the following amino acids were successively reacted with the growing peptide chain: Fmoc-S-trityl-L-cysteine, Fmoc-O-t-butyl-L-threonine, $N^\alpha$-Fmoc-$N^{68}$-Boc-L-lysine, $N^\alpha$-Fmoc-$N^{in}$-Boc-D-tryptophan, Fmoc-L-phenylalanine, Fmoc-S-trityl-L-cysteine, Fmoc-O-t-butyl-D-serine, Fmoc-O-t-butyl-D-tyrosine, $N^\alpha$-Fmoc-Norleucine, Fmoc-O-t-butyl-D-serine, Bromoacetic acid. After completion of bromoacetic acid coupling to peptidyl resin, (3 eq) N-Boc-N-methylethylenediamine was added in NMP and mixed for two hours then washed 3 times with DMF and 3 times with DCM. Camptothecin chloroformate from EXAMPLE 1 was added to the resin and mixed overnight, washed with copious amounts of DMF followed by methanol. After a final filtration the derivatized resin was air dried overnight

EXAMPLE 14

Preparation of camptothecin-carbonyl-N-(N-methyl-2-aminoethyl)-glycine-D-Ser-Nle-D-Tyr-D-Ser-cyclo [Cys-Phe-D-Trp-Lys-Thr-Cys]-Thr-amide (SEQ ID NO: 40)

The camptothecin-peptide resin prepared in EXAMPLE 13 (0.063 mmol) was placed in a RB flask to which was added 15 mL of a solution of trifluoroacetic acid (TFA) containing water (2.5%), 1,2-ethanedithiol (2.5%), and triisopropylsilane (1%). The suspension was agitated (2 h), filtered and washed several times with TFA. The TFA was evaporated in vacuo and ether added to the resulting oil to give a yellow powder that was then dissolved in 60% acetic acid (250 mL). A concentrated solution of iodine in methanol was added dropwise with vigorous stirring until a permanent brown coloration was formed whereupon excess iodine was removed by addition of a small quantity of ascorbic acid.

The solution was reduced to a volume of around 10 mL in vacuo and the crude camptothecin peptide purified by preparative reverse phase high pressure liquid chromatography (RP-HPLC) on a column (21.4×250 mm) of C-18 bonded silica (Dynamax 300, 8 μm). A linear gradient elution system at a flow rat of 20 mL/min was employed: buffer A consisted of 0.1% TFA and buffer B, 0.1% TFA in 80% MeCN; 20% B to 50% B was increased at 1% per min. The separation was monitored at 280 nm. The fractions containing the pure product as evidenced by analytical HPLC were pooled, concentrated in vacuo and subjected to lyophilization. The peptide was obtained as a fluffy yellow powder of constant weight by lyophilization from aqueous acetic acid. Correct composition was demonstrated by amino acid analysis of an acid hydrolysate and matrix assisted laser desorption mass spectrometry.

EXAMPLE 15 di-tert-butyloxycarbonyl-His-Leu-Gln-Ile-Gln-Pro-tert-butyloxycarbonyl-Trp-tert-butyl-Tyr-Pro-Gln-Ile-tert-butyl-Ser-N-e-camptothecin-carbonyl-N-(N-2-aminoethyl)-glycine-Lys-tert-butyl-Ser-Rink-amide-resin (SEQ ID NO: 20)

Rink amide MBHA polystyrene resin (0.063 mmol) resin, 100-200 mesh, Novabiochem, San Diego, Calif.) was added to the reaction vessel of a CS136 automatic peptide synthesizer (CS Bio, Inc., San Carlos, Calif.) and swollen in DMF for approximately 1 hour. The resin was filtered and an excess of 20% piperidine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Serine(tBut) (0.188 mmol), diisopropylcarbodiimide (DIC) (0.188 mmol), and N-hydroxybenzotriazole monohydrate (HOBt) (0.188 mmol) were all dissolved in DMF and added to the resin which was mixed (1 h) followed by washing 4 times with DMF.

The Fmoc group was again removed by treatment with 20% piperidine/DMF solution and, following the same general coupling procedures, the following amino acids were successively reacted with the growing peptide chain: Fmoc-N-e-1(4,4-dimethyl-2,6-dioxocyclohex-1-ylidene)3-3methyl-butyl-L-Lysine, Fmoc-O-t-butyl-L-Serine, $N^\alpha$-Fmoc—L-Isoleucine, N-Fmoc-L-Glutamine, N-Fmoc-L-Proline, N-Fmoc-O-Trityl-L-Tyrosine, $N^\alpha$-Fmoc-$N^{in}$-Boc-L-tryptophan, N-Fmoc-L-Proline, N-Fmoc-L-Glutamine, $N^\alpha$-Fmoc—L-Isoleucine, N-Fmoc-L-Glutamine, $N^\alpha$-Fmoc-Leucine, Boc-O-t-butyl-L-Histidine.

The protected peptide resin was then treated 3 times (3 min each) with a 2% solution of hydrazine hydrate in DMF in order to remove the N-e-1-(4,4-dimethyl-2,6-dioxocyclohex-1-ylidene)3-methyl-butyl (ivDde) group on the lysine residue. The free e-amino group was then coupled with bromoacetic acid followed by addition of N-Boc-N-ethylenediamine (3 eq, 12 h) in NMP. Camptothecin chloroformate from EXAMPLE 1 was added to the resin and mixed overnight, washed with copious amounts of DMF followed by methanol. After a final filtration the derivatized resin was air dried overnight.

EXAMPLE 16

Preparation of Camptothecin Derivative of Phage Peptide p147:

His-Leu-Gln-Ile-Gln-Pro-Trp-Tyr-Pro-Gin-Ile-Ser-N-e-camptothecin-carbonyl-N-(N-2-aminoethyl)-glycine-Lys-Ser-$NH_2$ (SEQ ID NO: 20)

The camptothecin-peptide resin prepared in EXAMPLE 15 (0.063 mmol) was placed in a RB flask to which was added 15 mL of a solution of trifluoroacetic acid (TFA) containing water (2.5%), 1,2-ethanedithiol (2.5%), and triisopropylsilane (1%). The suspension was agitated (5 h), filtered and washed several times with TFA. The TFA was evaporated in vacuo and ether added to the resulting oil to give a yellow powder which was purified by preparative reverse phase high pressure liquid chromatography (RP-HPLC) on a column (21.4×250 mm) of C-18 bonded silica (Dynamax 300, 8 μm). A linear gradient elution system at a flow rat of 20 mL/min was employed: buffer A consisted of 0.1% TFA and buffer B, 0.1% TFA in 80% MeCN; 20% B to 50% B was increased at 1% per min. The separation was monitored at 280 nm. The fractions containing the pure product as evidenced by analytical HPLC were pooled, concentrated in vacua, and subjected to lyophilization. The peptide was obtained as a fluffy yellow powder of constant weight by lyophilization from aqueous acetic acid. Correct composition was demonstrated by amino acid analysis of an acid hydrolysate and matrix assisted laser desorption mass spectrometry.

EXAMPLE 17

Preparation of N-carboxyanhydride of O-t-butyl-D,L-serine

O-t-butyl-D-serine (0.0062 mol) and O-t-butyl-L-serine (0.0062 mol) were suspended in 55 mL anhydrous tetrahydrofuran (THF) under nitrogen atmosphere. Phosgene (0.025 mol) was added to suspension and the suspension was refluxed for 15 minutes. Solvent and excess phosgene were evaporated and the resulting oil was dissolved in 10 mL THF then added to 600 mL Hexanes and crystallized at −20° C.

EXAMPLE 18

Preparation of Camptothecin-carbonyl-N-(2-aminoethyl)-glycine-[D or L O-tert-butyl-Ser]$_{15}$-D-tert-butyl-Ser-Norleucine-D-tert-butyl-Tyr-D-tert-butyl-Ser-S-trityl-Cys-Phe-D-Trp-epsilon-tert-butyloxycarbonyl-Lys-tert-butyl-Thr-S-trityl-Cys-tert-butyl-Thr-Rink-amide-resin (SEQ ID NO: 21, and SEQ ID NO: 23-SEQ ID NO 36)

Rink amide MBHA polystyrene resin (0.063 mmol) [4-(2', 4'-dimethoxyphenyl-Fmoc-(aminomethyl)phenoxyacetamido-norleucyl-methylbenzhydrylamine resin, 100-200 mesh, Novabiochem, San Diego, Calif.] was added to the reaction vessel of a CS136 automatic peptide synthesizer (CS Bio, Inc., San Carlos, Calif.) and swollen in DMF for approximately 1 hour. The resin was filtered and an excess of 20% piperidine in DMF was added and mixed for 2 minutes. The resin was filtered and again an excess amount of 20% piperidine added and mixed for 20 minutes to ensure complete removal of the resin Fmoc group. After deprotection, the resin was washed 4 times with DMF and then the first protected amino acid, Fmoc-Thr(tBut) (0.188 mmol), diisopropylcarbodiimide (DIC) (0.188 mmol), and N-hydroxybenzotriazole monohydrate (HOBt) (0.188 mmol) were all dissolved in DMF and added to the resin which was mixed (1 h) followed by washing 4 times with DMF.

The Fmoc group was again removed by treatment with 20% piperidine/DMF solution and, following the same general coupling procedures, the following amino acids were successively reacted with the growing peptide chain: Fmoc-S-trityl-L-cysteine, Fmoc-O-t-butyl-L-threonine, N$^\alpha$-Fmoc-N$^\epsilon$-Boc-L-lysine, N$^\alpha$-Fmoc-N$^{in}$-Boc-D-tryptophan, Fmoc-L-phenylalanine, Fmoc-S-trityl-L-cysteine, Fmoc-O-t-butyl-D-serine, Fmoc-O-t-butyl-D-tyrosine, N$^\alpha$-Fmoc-Norleucine, Fmoc-O-t-butyl-D-serine. At this point the N-terminal Fmoc group was removed, the resin washed several times with DMF, then the resin was transferred to a 100 mL RB flask. O-tert-butyl-Serine NCA (1.5 g) was dissolved in anhydrous DMF and added to the peptidyl resin and the suspened resin was shaken overnight at 40° C. The resin was filtered and washed several times with DMF then placed back on the CS Bio synthesizer. Bromoacetic acid was then coupled to the N-terminal serine in DCM/DIC. After completion of Bromoacetic acid coupling to peptidyl resin, (3 eq) N-Boc-ethylenediamine was added in NMP and mixed for two hours then washed 3 times with DMF and 3 times with DCM. Camptothecin chloroformate from EXAMPLE 1 was added to the resin and mixed overnight, washed with copious amounts of DMF followed by methanol. After a final filtration the derivatized resin was air dried overnight

EXAMPLE 19

Preparation of camptothecin-carbonyl-N-(2-aminoethyl)-glycine-[Poly-D,L-Ser]-D-Ser-Nle-D-Tyr-D-Ser-cyclo[Cys-Phe-D-Trp-Lys-Thr-Cys]-Thr-amide (SEQ ID NO: 22)

The camptothecin-peptide resin prepared in EXAMPLE 18 (0.063 mmol) was placed in a RB flask to which was added 15 mL of a solution of trifluoroacetic acid (TFA) containing water (2.5%), 1,2-ethanedithiol (2.5%), and triisopropylsilane (1%). The suspension was agitated (2 h), filtered, and washed several times with TFA. The TFA was evaporated in vacuo and ether added to the resulting oil to give a yellow powder that was then dissolved in 60% acetic acid (250 mL). A concentrated solution of iodine in methanol was added dropwise with vigorous stirring until a permanent brown coloration was formed whereupon excess iodine was removed by addition of a small quantity of ascorbic acid.

The solution was reduced to a volume of around 10 mL in vacuo and the crude camptothecin peptide purified by preparative reverse phase high pressure liquid chromatography (RP-HPLC) on a column (21.4×250 mm) of C-18 bonded silica (Dynamax 300, 8 µm). A linear gradient elution system at a flow rate of 20 mL/min was employed: buffer A consisted of 0.1% TFA and buffer B, 0.1% TFA in 80% MeCN; 20% B to 50% B was increased at 1% per min. The separation was monitored at 280 nm. The fractions containing the pure product as evidenced by analytical HPLC were pooled, concentrated in vacuo, and subjected to lyophilization. The peptide was obtained as a fluffy yellow powder of constant weight by lyophilization from aqueous acetic acid. Correct composition was demonstrated by amino acid analysis of an acid hydrolysate and matrix assisted laser desorption mass spectrometry.

EXAMPLE 20

In Vivo and In Vitro Use of Conjugate Carbamate Compounds

Conjugate compounds with a carbamate linker were tested in vitro and in vivo for release rate of the cytotoxic agent. A carbamate linker was chosen because it is reasonably stable in plasma compared, for example, to commonly used ester-type linkages. We also tested carbamate compounds containing an intramolecular cyclic moiety that allows adjustment of the release rate of the alcoholic component of the carbamate culminating in the release of an attached alcohol derivative and formation of a cyclic urea which can be utilized to control release rates of suitable cytotoxins (FIG. 1). It is known that the pKa value of the leaving alcohol of a carbamate is important for the stability of the prodrug, therefore, we chose two different chemically suitable cytotoxic agents each containing one hydroxyl group with signicantly different pKa values. One cytotoxic agent was the topoisomerase I inhibitor, camptothecin, which bears a tertiary hydroxyl group in ring position 20 (FIG. 1) with a pKa of approximately 18. The other cytotoxic agent was the tubulin-binding agent, combretastatin, which has one phenolic hydroxyl group attached to an aromatic ring, thus exhibiting a much lower pKa value of approximately 10.3.

All peptide conjugates shown in Table 1 were synthesized totally on Rink amide resin support using the standard FMOC (9-fluorenylmethoxycarbonyl) protection/deprotection strategy employing simple DIC couplings and HBTU activation as a second step only if a Kaiser test was positive (as described above). Once the peptide portion of the conjugate was complete, bromoacetic acid was coupled to the N-terminus using DIC/DCM. After washing the resin, a 5 M excess of N-BOC-ethylenediamine (or the appropriate protected diamine) in NUT was added and mixed for 1 h. Seperately, camptothecin (200 mg; Aldrich) and DMAP (400 mg) in anhydrous DCM (40 mL) were mixed and cooled to 0° C. To this suspension was added 20% phosgene in toluene (600 uL) and the mixture was allowed to react for about 45 min. After solvent evaporation, the powder was suspended in DCM (40 mL) and added to the peptidyl resin bearing the free secondary amine and allowed to react overnight followed by washing several times with DMF, DCM, and methanol. The peptide was then cleaved from the resin for 2 h using the standard acid mixture TFA:H$_2$0:EDT:TIS, 95:2:2:1. After cleavage, the conjugate was precipitated 4 times in ethyl ether, dissolved in 60% HOAC, and cyclized with iodine in methanol. It was then subjected to preparative chromatography and characterized by MS and amino acid analysis. All peptides were obtained in at least 90+% purity and yields were around 35% theoretical. Full retention of conjugate agonists potencies relative to somatostatin itself was demonstrated by their ability to inhibit gonadotropin releasing hormone (GNRH)-stimulated GH release from monolayer cultures of rat pituitary cells, an assay system that has been shown to correlate well with binding affinity to the human type 2 somatostatin receptor (see, e.g., Raynor et al., Mol. Pharmacol. 43:838, 1993). Inhibitory potencies (IC50's) of the conjugates shown in Table 2 ranged from 0.26 to 0.49 nM compared to 0.63 nM for somatostatin-14 itself. This retention of full affinity is due to the employment of the N-terminal Nle-d-Tyr-d-Ser tripeptide extension of the cyclic somaostatin portion of the conjugate that we have found generally allows large groups to be attached with little to no loss of affinity.

TABLE 2

Agonist activity, cytotoxicity, and buffer and serum half-life of compounds 1-6 and control compounds

| Compounds | Cytotoxicity IC$_{50}$, nM$^a$ IMR-32 Cells | Half Life Phosphate Buffer (Hours) | Half-Life Rat Serum (Hours) | Growth Hormone Inhibition IC$_{50}$, nM$^a$ |
|---|---|---|---|---|
| 1 | 374 ± 18 | Stable$^a$ | 106 | 0.32 ± 0.02 |
| 2 | 54.2 ± 6 | 123 | 18 | 0.27 ± 0.02 |
| 3 | 571 ± 48 | Stable | 59 | 0.30 ± 0.04 |
| 4 | >1000 | Stable | 72 | 0.26 ± 0.03 |
| 5 | >1000 | na | na | 0.49 ± 0.1 |
| 6 | 2.79 ± 0.33 | 31 | 4 | 0.31 ± 0.1 |
| Camptothecin | 2.21 ± 0.44 | na | na | na |
| Combretastatin | 4.36 | na | na | na |

TABLE 1

Structures of camptothecin and combretastatin conjugates containing various BINAR linking groups.

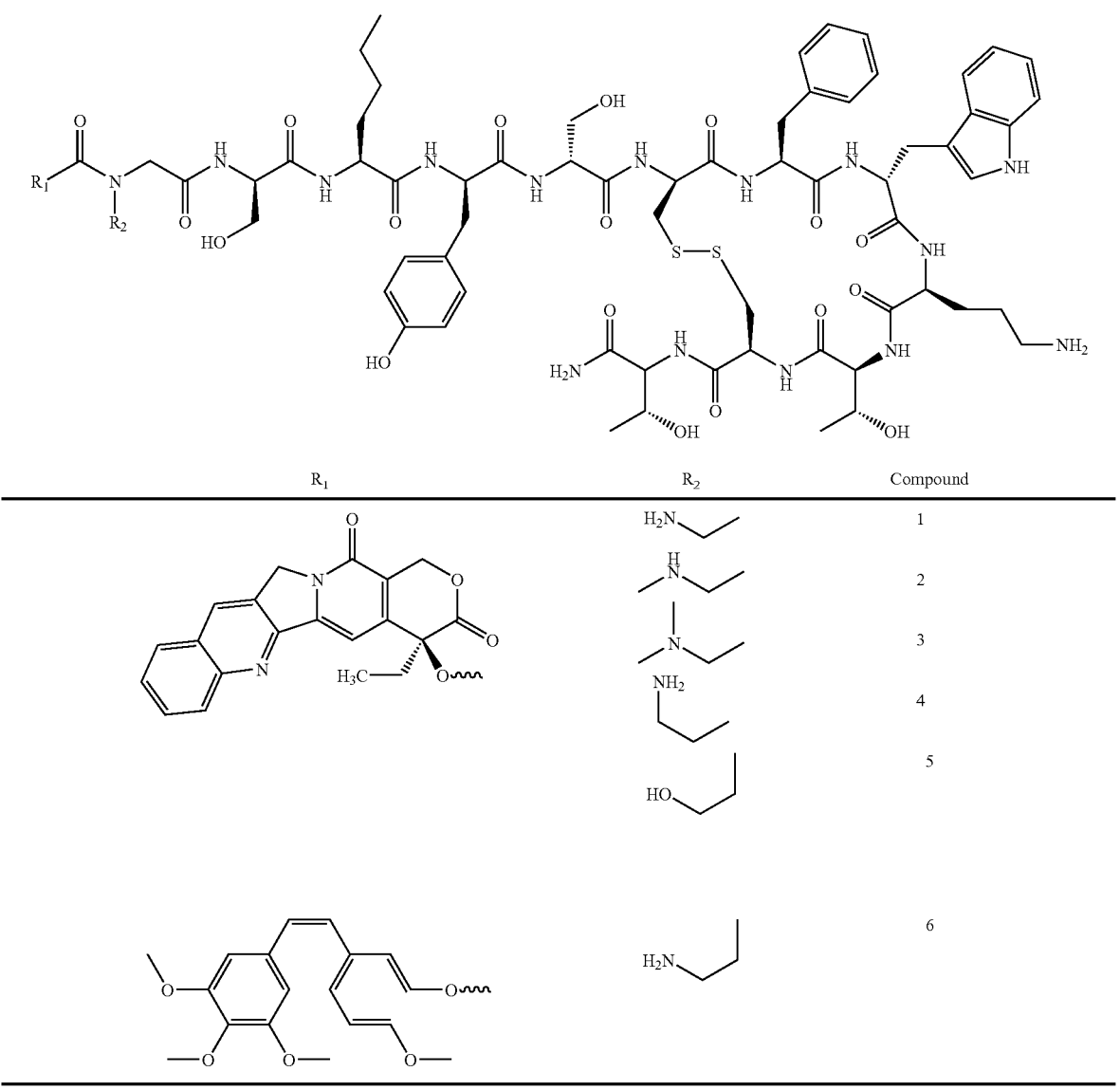

TABLE 2-continued

Agonist activity, cytotoxicity, and buffer and serum
half-life of compounds 1-6 and control compounds

| Compounds | Cytotoxicity $IC_{50}$, $nM^a$ IMR-32 Cells | Half Life Phosphate Buffer (Hours) | Half-Life Rat Serum (Hours) | Growth Hormone Inhibition $IC_{50}$, $nM^a$ |
|---|---|---|---|---|
| SRIF (1-14) | na[b] | na | 2-5 minutes | 0.63 ± 0.029 |

[a]Experiment carried out for 50 h.
[b]Somtostatin analogues were non-toxic to IMR32 cells at up to $10^{-5}$ M concentrations.

Each peptide conjugate was subjected to phosphate buffer and rat serum stability studies. The analogues were incubated in either 0.1 M phosphate buffer or fresh rat serum at 37° C. and aliquots were taken at different time points and examined by HPLC. Compounds 1, 3, and 4 showed complete buffer stability for the length of the experiment (50 h; Table 2). Compound 2 was less stable in buffer with a half-life of around 120 h, while compound 6 was the least stable with a half-life of only 30 h in buffer. In rat serum, this same trend was evident, except that there was clearly a catabolic effect of serum on the stability of the compounds. Compounds 1, 3, and 4 were again the most stable, while compound 2's half-life was 18 h and combretastatin compound 6, which contains the phenolic hydroxyl, was least stable with a 4 h half-life.

Figure 2:
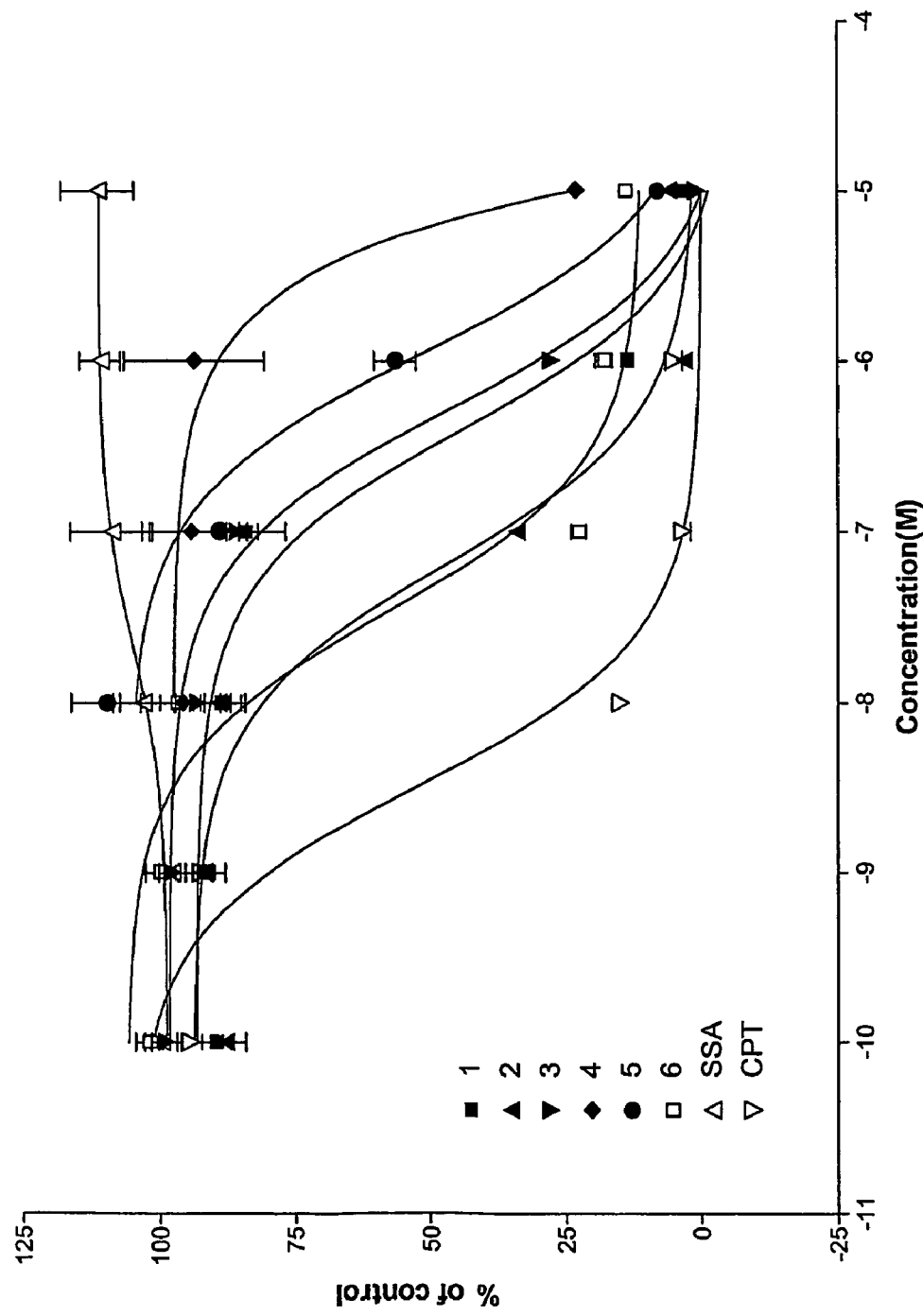
FIG. 2 is a graph demonstrating the dose-response curve for conjugates 1-6 and showing the ability of conjugates 1-6 to kill somatostatin receptor subtype 2 (SSTR2) positive IMR-32 cells after incubation for 3 days using a cell viability MTT assay.

The cytotoxic activities of these conjugates were measured using a standard MTT assay kit (Promega Corporation, Madison, Wis.). Each compound was incubated for 3 days with human neuroblastoma IMR32 cells (somatostatin receptor overexpression) at different concentrations in quadruplate and IC50's were generated from the dose-response curves (FIG. 2). Although the combretastatin-ethlylenediamine BINAR compound 6 was the most cytotoxic, after reviewing the stability data in buffer, it is evident that 50% of this conjugate is free cytoxin after 3 days and perhaps more since cell media will contain some enzymes. The N-Me-ethylenediamine camptothecin conjugate 2 was the second most potent. After 3 days, more than 80% of this conjugate was still intact The next most potent was the ethlylenediamine compound 1. This analogue demonstrated complete stability in phosphate buffer, but was seven times less potent than compound 2 and slightly more active than compound 3 even though it was more stable in serum. This property is likely due to compound 1's ability to form a cyclic urea while compound 3 is unable to form this same species.

In preliminary tumor bearing animal studies, compounds 1 and 2 appear to be equally effective at inducing a cytotoxic effect in the tumor after repeated intraperitoneal administration. Compounds based on N,N-dimethyethylenediamine, diaminopropyl, and 2-hydroxyethylamine BINAR groups (FIG. 2; Table 2) were essentially inactive presumably due to lack of release of any free cytotoxic agent intra- or extracellularly. The lead camptothecin conjugate 2 was able to significantly stabilize the growth of transplanted NCI-H69 small cell lung carcinomas (expression of SSTR2) in nude mice at doses far below the maximum tolerated equivalent doses of camptothecin alone. The data suggest not only a chemical component to the release rate of the alcohol but also some enzymatic component.

The value of the BINAR linking strategy lies both in its ability to be adjusted to accommodate ideal release rates for various types of alcohol containing groups and its ease of incorporation onto a peptide free amino group by simple solid-phase chemistries. The chemistry for introducing the groups is well suited for solid phase synthesis and is easily adapted for many different peptides, therapeutic agents, and cytotoxins. Although this strategy is readily applied to the N-terminus, it can also be applied to an orthogonally protected side chain as well should this be necessary for preservation of peptide binding affinity. With the present camptothecin conjugates, high cytotoxicity was achieved with compounds 1 and 2 (FIG. 2; Table 2) even though they were very stable to cell media incubation conditions. High concentrations of intact peptide conjugate will be specifically bound to tumor cells whereupon internalization would take place. Furthermore, the conjugates are highly soluble and tissue clearance rates and routes can be readily further adjusted by altering the hydrophilicity of the peptide component, as described above. If the peptide conjugate remains reasonably intact during clearance, then toxic side effects should be much reduced.

EXAMPLE 21

Preparation of Camptothecin-carbonyl-N-aminoethyl-glycine-S-trityl-Cys-Rink-amide-resin Rink amide [4-(2',4'-dimethoxyphenyl-Fmoc-(aminomethyl)phenoxyacetamido-norleucyl-methylbenzhydrylamine resin (0.063 mmole), 100-200 mesh (Novabiochem, San Diego, Calif.) was added to the reaction vessel of a CS136 automatic peptide synthesizer (CS Bio, Inc., San Carlos, Calif.) and swollen in dimethylformamide (DMF) for approximately 1 h. The resin was filtered and an excess of 20% piperidine in DMF was added and mixed (2 min). The resin was filtered and again an excess amount of 20% piperidine added and mixed (20 min) to ensure complete removal of the resin Fmoc group. After deprotection, the resin was washed 4 times with DMF and then the first protected amino acid, Fmoc-S-trityl-L-cysteine (0.188 mmol), diisopropylcarbodiimide (DIC) (0.188 mmol), and N-hydroxybenzotriazole monohydrate (HOBt) (0.188 mmol) were all dissolved in DMF/DCM and added to the resin, which was mixed for 1 h, followed by washing 4 times with DMF.

The Fmoc group was again removed by treatment with 20% piperidine/DMF solution and, following the same general coupling procedures, Fmoc-N-(2-Boc-aminoethyl)glycine (Neosystem) was added. The Fmoc group was removed and the peptidyl resin washed several times with DCM. Camptothecin chloroformate from EXAMPLE 1 was added to the resin and mixed overnight, then washed with copious amounts of DMF followed by methanol. After a final filtration the derivatized resin was air dried overnight.

Preparation of camptothecin-carbonyl-N-(2-aminoethyl)-glycine-Cys-amide

The camptothecin-peptide resin prepared in EXAMPLE 21 (0.063 mmol) was placed in a round bottomed flask to which was added 15 mL of a solution of trifluoroacetic acid (TFA) containing water (2.5%), 1,2-ethanedithiol (2.5%), and triisopropylsilane (1%). The suspension was agitated (2 h), filtered, and washed several times with TFA. The TFA was evaporated in vacuo and ether added to the resulting oil to give a yellow powder that was then dissolved in 60% acetic acid (15 mL).

The crude camptothecin peptide was purified by preparative reverse phase high pressure liquid chromatography (RP-HPLC) on a column (21.4×250 mm) of C-18 bonded silica (Dynamax 300, 8 μm). A linear gradient elution system at a flow rat of 20 mL/min was employed: buffer A consisted of 0.1% TFA and buffer B, 0.1% TFA in 80% MeCN; 20% B to 50% B was increased at 1% per min. The separation was monitored at 280 nm. The fractions containing the pure product, as identified by analytical HPLC, were pooled, concentrated in vacuo, and subjected to lyophilization. The peptide was obtained as a fluffy yellow powder of constant weight by lyophilization from aqueous acetic acid. Correct composition, as shown below, was demonstrated by matrix assisted laser desorption mass spectrometry.

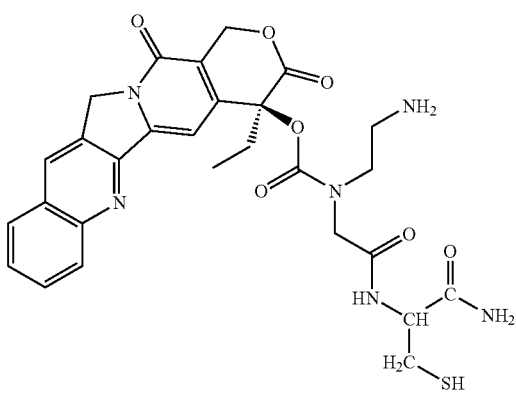

EXAMPLE 23

Preparation of Camptothecin-carbonyl-N-aminoethyl-glycine-Phe(benzophenone)-amide-resin Rink amide [4-(2',4'-dimethoxyphenyl-Fmoc-(aminomethyl)phenoxyacetamido-norleucyl-methylbenzhydrylamine resin (0.063 mmole), 100-200 mesh (Novabiochem, San Diego, Calif.) was added to the reaction vessel of a CS136 automatic peptide synthesizer (CS Bio, Inc., San Carlos, Calif.) and swollen in dimethylformamide (DMF) for approximately 1 h. The resin was filtered and an excess of 20% piperidine in DMF was added and mixed (2 min). The resin was filtered and again an excess amount of 20% piperidine added and mixed (20 min) to ensure complete removal of the resin Fmoc group. After deprotection, the resin was washed 4 times with DMF and then the first protected amino acid, Fmoc-L-p-benzoyl-Phenylalanine (0.188 mmol), diisopropylcarbodiimide (DIC) (0.188 mmol), and N-hydroxybenzotriazole monohydrate (HOBt) (0.188 mmol) were all dissolved in DMF/DCM and added to the resin, which was mixed for 1 h, followed by washing 4 times with DMF.

The Fmoc group was again removed by treatment with 20% piperidine/DMF solution and, following the same general coupling procedures, Fmoc-N-(2-Boc-aminoethyl)glycine (Neosystem) was added. The Fmoc group was removed and the peptidyl resin washed several times with DCM. Camptothecin chloroformate from EXAMPLE 1 was added to the resin and mixed overnight, then washed with copious amounts of DMF followed by methanol. After a final filtration the derivatized resin was air dried overnight.

EXAMPLE 24

Preparation of camptothecin-carbonyl-N-(2-aminoethyl)-glycine-p-Benzoyl-phenylalanine-amide The camptothecin-peptide resin prepared in EXAMPLE 23 (0.063 mmol) was placed in a round bottomed flask to which was added 15 mL of a solution of trifluoroacetic acid (TFA) containing water (2.5%), and triisopropylsilane (1%). The suspension was agitated for 2 h, filtered, and washed several times with TFA. The TFA was evaporated in vacuo and ether added to the resulting oil to give a yellow powder that was then dissolved in 60% acetic acid (15 mL).

The crude camptothecin peptide was purified by preparative reverse phase high pressure liquid chromatography (RP-HPLC) on a column (21.4×250 mm) of C-18 bonded silica (Dynamax 300, 8 μm). A linear gradient elution system at a flow rat of 20 mL/min was employed: buffer A consisted of 0.1% TFA and buffer B, 0.1% TFA in 80% MECN; 20% B to 50% B was increased at 1% per min. The separation was monitored at 280 nm. The fractions containing the pure product, as identified by analytical HPLC, were pooled, concentrated in vacuo, and subjected to lyophilization. The peptide was obtained as a fluffy yellow powder of constant weight by lyophilization from aqueous acetic acid. Correct composition, as shown below, was demonstrated by matrix assisted laser desorption mass spectrometry.

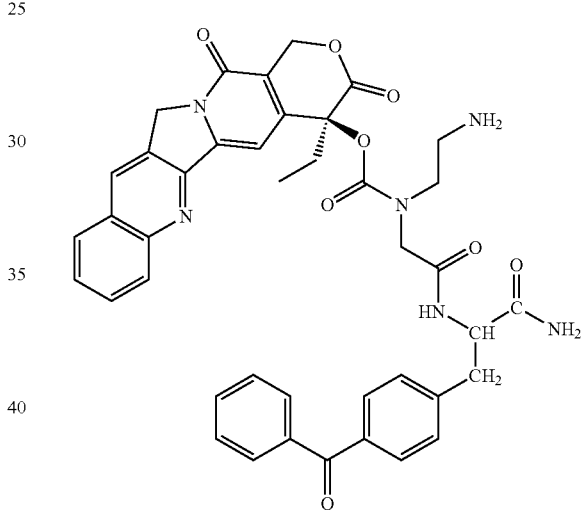

Other Embodiments

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are intended to be encompassed in the scope of the present invention.

All publications and patent applications mentioned in this specification are herein incorporated by reference to the same extent as if each independent publication or patent application was specifically and individually indicated to be incorporated by reference.

What is claimed is:

1. A compound represented by the following formula:

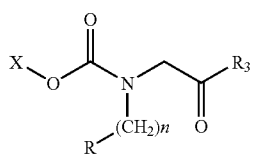

wherein:

X is camptothecin, homocamptothecin, colchicine, thiocolchicine, combretastatin, dolastatin, doxorubicin, methotrexate, podophyllotoxin, rhizoxin, rhizoxin D, a taxol, paclitaxel, CC1065, or a maytansinoid;

n is an integer from 0 to 6, wherein $(CH_2)_n$ is an alkyl or a cyclic group;

R is $N(R_1R_2)$, $OR_1$, or $SR_1$, wherein $R_1$ and $R_2$ are, independently, hydrogen or a straight or branched chain lower alkyl group having fewer than 11 carbon atoms, and wherein $R_3$ is a $NH(CH_2)_mSH$ group and m=2 to 6, D or L cysteine, a benzophenone, an OH group, or is NH-Y-Z-Q wherein:

Y is a hydrophilic spacer sequence selected from the group consisting of a peptide that increases the hydrophilic biodistribution of said compound and a hydrophilic polymer, or is omitted, wherein:

said peptide that increases the hydrophilic biodistribution of said compound has the formula U(V-V)n, wherein U is D-Pro, L-Pro, D-4-OH-Pro, L-4-OH-Pro, Sarcosine, Lys, Ore, Dab, Dap, 4-$NH_2$-Phe, or ($NH_2$—$(CH_2)_m$—COOH), where m=2-10, inclusive, or is deleted; each V is independently selected from the group consisting of: D-Ser, L-Ser, D-Thr, L-Thr, D-Gln, L-Gln, D-Asn, L-Asn, D-4-OH-Pro, and L-4 hydroxy-Pro; and n=1-50, inclusive, and said hydrophilic polymer is selected from the group consisting of polyethylene glycol, polyvinyl acetate, polyvinyl alcohol, HPMA (N-(2-hydroxypropyl) methacrylamide) or HPMA copolymers, α, β-poly (N-hydroxyethyl)-DL-aspartamide (PHEA), and α, β-poly(N-hydroxypropyl)-DL-aspartamide;

Z is a linking peptide that is bonded to Q at the N-terminus or at a compatible side-chain amino group of Q or is omitted, wherein Z has the formula:

A-B-C-E-F, wherein:
A is D-Lys, D-Tyr, D-Ser, or L-Ser, or is deleted;
B is D-Lys or D-Tyr, or is deleted;
C is Lys, Ser, hSer, Thr, Nle, Abu, Nva, (2, 3, or 4) 3-pyridyl-Ala (Pal), Orn, Dab, Dap, 4-NH$_2$-Phe, D-4-OH-Pro, or L-4-OH-Pro, or is deleted;
E is D-Lys, D-Tyr, D-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; and
F is D-Lys, D-Tyr, D-Ser, L-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln;
provided that when A, B, C, and E are Tyr, Tyr, Lys, and Tyr, respectively, F is not Lys; and when A, B, C, and E are Lys, Tyr, Lys, and Tyr, respectively, F is not Tyr or Lys; and when A and B are deleted, and C and E are Lys and Tyr, respectively, F is not Tyr or Lys; and
Q is a targeting moiety selected from a somatostatin peptide, a bombesin peptide, or a vasoactive intestinal peptide (VIP).

2. A compound represented by the following formula:

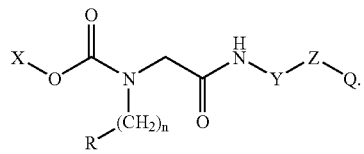

wherein:
X is a cytotoxic agent selected from camptothecin, homocamptothecin, colchicine, thiocolchicine, combretastatin, dolastatin, doxorubicin, methotrexate, podophyllotoxin, rhizoxin, rhizoxin D, a taxol, paclitaxel, CC1065, and a maytansinoid;
n is an integer from 0 to 6, wherein $(CH_2)_n$ is an alkyl or a cyclic group;
R is $N(R_1R_2)$, $OR_1$, or $SR_1$, wherein $R_1$ and $R_2$ are, independently, hydrogen or a straight or branched chain lower alkyl group having fewer than 11 carbon atoms;
Y is a hydrophilic spacer sequence selected from the group consisting of a peptide that increases the hydrophilic biodistribution of said compound and a hydrophilic polymer, or is omitted, wherein:
said peptide that increases the hydrophilic biodistribution of said compound has the formula U(V-V)n, wherein U is D-Pro, L-Pro, D-4-OH-Pro, L-4-OH-Pro, Sarcosine, Lys, Ore, Dab, Dap, 4-NH$_2$-Phe, or (NH$_2$—(CH$_2$)$_m$—COOH), where m=2-10, inclusive, or is deleted; each V is independently selected from the group consisting of: D-Ser, L-Ser, D-Thr, L-Thr, D-Gln, L-Gln, D-Asn, L-Asn, D-4-OH-Pro, and L-4 hydroxy-Pro; and n=1-50, inclusive, and
said hydrophilic polymer is selected from the group consisting of polyethylene glycol, polyvinyl acetate, polyvinyl alcohol, HPMA (N-(2-hydroxypropyl) methacrylamide) or HPMA copolymers, α, β-poly (N-hydroxyethyl)-DL-aspartamide (PHEA), and α, β-poly(N-hydroxypropyl)-DL-aspartamide;

Z is a linking peptide, that is bonded to Q at the N-terminus or at a compatible side-chain amino group of Q or is omitted, wherein Z has the formula:

A-B-C-E-F, wherein:
A is D-Lys, D-Tyr, D-Ser, or L-Ser, or is deleted;
B is D-Lys or D-Tyr, or is deleted;
C is Lys, Ser, hSer, Thr, Nle, Abu, Nva, (2, 3, or 4) 3-pyridyl-Ala (Pal), Orn, Dab, Dap, 4-NH$_2$-Phe, D-4-OH-Pro, or L-4-OH-Pro, or is deleted;
E is D-Lys, D-Tyr, D-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln; and
F is D-Lys, D-Tyr, D-Ser, L-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln;
provided that when A, B, C, and E are Tyr, Tyr, Lys, and Tyr, respectively, F is not Lys; and when A, B, C, and E are Lys, Tyr, Lys, and Tyr, respectively, F is not Tyr or Lys; and when A and B are deleted, and C and E are Lys and Tyr, respectively, F is not Tyr or Lys; and
Q is a targeting moiety selected from a somatostatin peptide, a bombesin peptide, or a vasoactive intestinal peptide (VIP).

3. The compound of claim 2, wherein said hydrophilic spacer sequence is said peptide that increases the hydrophilic biodistribution of said compound.

4. The compound of claim 3, wherein at least one V is a D-amino acid.

5. The compound of claim 3, wherein V is independently D-Ser or L-Ser.

6. The compound of claim 2, wherein said hydrophilic spacer sequence is said hydrophilic polymer.

7. The compound of claim 2, wherein said somatostatin peptide, bombesin peptide, or VIP targets said compound to a cell or tissue in the body of a mammal.

8. The compound of claim 7, wherein said somatostatin peptide, bombesin peptide, or VIP is derived from a phage-display library, or comprises conservative substitutions thereof.

9. The compound of claim 7, wherein said cell or tissue comprises a cancer cell, a white blood cell, cardiac tissue, brain tissue, or a tubercle infected with tuberculosis, or wherein said tissue is a tumor or a proliferative angiogenic blood vessel.

10. The compound of claim 9, wherein said blood vessel is in the eye.

11. The compound of claim 2, wherein Q is said somatostatin peptide.

12. The compound of claim 2, wherein Q is said bombesin peptide.

13. The compound of claim 2, wherein Z is D-Ser-Nle-D-Ser-D-Ser, D-Ser-Lys-D-Ser-D-Ser, D-Ser-Lys-D-Tyr-D-Tyr, D-Ser-Lys-D-Tyr-D-Ser, D-Ser-Ser-D-Lys-D-Ser, D-Ser-Ser-D-Lys-Ser, D-Ser-Nle-D-Tyr-D-Ser, D-Ser-Pal-D-Tyr-D-Ser, D-Ser-Thr-D-Tyr-D-Ser, Lys-D-Ser-D-Ser, Ser-D-Lys-D-Ser, Ser-D-Lys-Ser, Nle-D-Tyr-D-Ser, Lys-D-Tyr-D-Ser, Pal-D-Lys-D-Ser, Thr-D-Tyr-D-Ser, D-Ser-D-Lys, D-Ser-D-Tyr, D-Lys-D-Lys, D-Lys-D-Tyr, D-Tyr-D-Lys, or wherein Z has the formula:

E-F, wherein:
- E is D-Lys, D-Tyr, D-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Gln, or L-Gln; and
- F is D-Lys, D-Tyr, D-Ser, L-Ser, D-4-OH-Pro, L-4-OH-Pro, 3-iodo-D-Tyr, 3-5 diiodo-D-Tyr, 3-astatine-D-Tyr, 3-5 astatine-D-Tyr, 3-bromo-D-Tyr, 3-5 dibromo-D-Tyr, D-Asn, L-Asn, D-Asp, L-Asp, D-Glu, L-Glu, D-Gln, or L-Gln.

14. The compound of claim 2, wherein R comprises 1 to 8 carbon atoms.

15. The compound of claim 1, wherein the $R_3$ group is used to attach a peptide, protein, or antibody to said compound.

16. The compound of claim 15, wherein $R_3$ is $NH(CH_2)mSH$ and m=2 to 6, and wherein said peptide, protein, or antibody is attached to said compound by a thiol reaction.

17. The compound of claim 15, wherein $R_3$ is a benzophenone and said peptide, protein, or antibody is attached to said compound by a photochemical reaction.

18. The compound of claim 17, wherein said benzophenone is p-benzoyl-phenylalanine.

19. A method of treating a disease comprising administering to a subject suffering from said disease a therapeutically effective amount of the compound of claim 2, wherein the disease is inflammatory bowel disease, rheumatoid arthritis, acromegaly, tuberculosis, a tumor of the lung, breast, brain, eye, prostate or colon, a tumor of neuroendocrine origin, an angiogenesis disease that causes inappropriate proliferation of blood vessels, retinal macular degeneration or diabetic neuropathy.

20. The compound of claim 2, wherein n=2 or 3.

21. The compound of claim 2 admixed with a pharmaceutically acceptable carrier, excipient, or salt.

22. The compound of claim 2, wherein Q is said VIP.

23. The compound of claim 2, wherein said somatostatin peptide is cyclo[Cys-Phe-D-Trp-Lys-Thr-Cys]-Thr-$NH_2$.

24. The compound of claim 2, wherein said cytotoxic agent is camptothecin, said linking peptide is D-Ser-Nle-D-Tyr-D-Ser, said targeting moiety is said somatostatin peptide having the sequence cyclo[Cys-Phe-D-Trp-Lys-Thr-Cys]-Thr-$NH_2$, said hydrophilic spacer sequence is omitted, and wherein n=2 and R is $N(R_1R_2)$, wherein $R_1$ and $R_2$ are hydrogen and methyl, respectively.

25. The compound of claim 24 admixed with a pharmaceutically acceptable carrier, excipient, or salt.

26. The method of claim 19, wherein said tumor of neuroendocrine origin is carcinoid syndrome.

27. The method of claim 19, comprising administering the compound of claim 25 to said subject.

28. The method of claim 19, wherein said subject is a mammal.

29. The method of claim 28, wherein said mammal is a human.

* * * * *

SEQUENCE LISTING

<160> NUMBER OF SEQ ID NOS: 48

<210> SEQ ID NO 1
<211> LENGTH: 4
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = D-Ser
<220> FEATURE:
<221> NAME/KEY: MISC_FEATURE
<222> LOCATION: (2)..(2)
<223> OTHER INFORMATION: Xaa = Nle
<220> FEATURE:
<221> NAME/KEY: MISC_FEATURE
<222> LOCATION: (3)..(3)
<223> OTHER INFORMATION: Xaa = D-Ser
<220> FEATURE:
<221> NAME/KEY: MISC_FEATURE
<222> LOCATION: (4)..(4)
<223> OTHER INFORMATION: Xaa = D-Ser

<400> SEQUENCE: 1

Xaa Xaa Xaa Xaa
1

<210> SEQ ID NO 2
<211> LENGTH: 4
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = D-Ser
<220> FEATURE:
<221> NAME/KEY: MISC_FEATURE
<222> LOCATION: (3)..(4)
<223> OTHER INFORMATION: Xaa = D-Ser

<400> SEQUENCE: 2

Xaa Lys Xaa Xaa
1

<210> SEQ ID NO 3
<211> LENGTH: 4
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = D-Ser
<220> FEATURE:
<221> NAME/KEY: MISC_FEATURE
<222> LOCATION: (3)..(4)
<223> OTHER INFORMATION: Xaa = D-Tyr

<400> SEQUENCE: 3

Xaa Lys Xaa Xaa
1

<210> SEQ ID NO 4
<211> LENGTH: 4
<212> TYPE: PRT

```
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = D-Ser
<220> FEATURE:
<221> NAME/KEY: MISC_FEATURE
<222> LOCATION: (3)..(3)
<223> OTHER INFORMATION: Xaa = D-Tyr
<220> FEATURE:
<221> NAME/KEY: MISC_FEATURE
<222> LOCATION: (4)..(4)
<223> OTHER INFORMATION: Xaa = D-Ser

<400> SEQUENCE: 4

Xaa Lys Xaa Xaa
1

<210> SEQ ID NO 5
<211> LENGTH: 4
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = D-Ser
<220> FEATURE:
<221> NAME/KEY: MISC_FEATURE
<222> LOCATION: (3)..(3)
<223> OTHER INFORMATION: Xaa = D-Lys
<220> FEATURE:
<221> NAME/KEY: MISC_FEATURE
<222> LOCATION: (4)..(4)
<223> OTHER INFORMATION: Xaa = Ser or D-Ser

<400> SEQUENCE: 5

Xaa Ser Xaa Xaa
1

<210> SEQ ID NO 6
<211> LENGTH: 4
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = D-Ser
<220> FEATURE:
<221> NAME/KEY: MISC_FEATURE
<222> LOCATION: (2)..(2)
<223> OTHER INFORMATION: Xaa = Nle
<220> FEATURE:
<221> NAME/KEY: MISC_FEATURE
<222> LOCATION: (3)..(3)
<223> OTHER INFORMATION: Xaa = D-Tyr
<220> FEATURE:
<221> NAME/KEY: MISC_FEATURE
<222> LOCATION: (4)..(4)
<223> OTHER INFORMATION: Xaa = D-Ser

<400> SEQUENCE: 6

Xaa Xaa Xaa Xaa
1

<210> SEQ ID NO 7
<211> LENGTH: 4
<212> TYPE: PRT
```

```
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = D-Ser
<220> FEATURE:
<221> NAME/KEY: MISC_FEATURE
<222> LOCATION: (2)..(2)
<223> OTHER INFORMATION: Xaa = Pal
<220> FEATURE:
<221> NAME/KEY: MISC_FEATURE
<222> LOCATION: (3)..(3)
<223> OTHER INFORMATION: Xaa = D-Tyr
<220> FEATURE:
<221> NAME/KEY: MISC_FEATURE
<222> LOCATION: (4)..(4)
<223> OTHER INFORMATION: Xaa = D-Ser

<400> SEQUENCE: 7

Xaa Xaa Xaa Xaa
1

<210> SEQ ID NO 8
<211> LENGTH: 4
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = D-Ser
<220> FEATURE:
<221> NAME/KEY: MISC_FEATURE
<222> LOCATION: (3)..(3)
<223> OTHER INFORMATION: Xaa = D-Tyr
<220> FEATURE:
<221> NAME/KEY: MISC_FEATURE
<222> LOCATION: (4)..(4)
<223> OTHER INFORMATION: Xaa = D-Ser

<400> SEQUENCE: 8

Xaa Thr Xaa Xaa
1

<210> SEQ ID NO 9
<211> LENGTH: 3
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(3)
<223> OTHER INFORMATION: Xaa = D-Ser

<400> SEQUENCE: 9

Lys Xaa Xaa
1

<210> SEQ ID NO 10
<211> LENGTH: 3
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = D-Lys
<220> FEATURE:
```

```
<221> NAME/KEY: MISC_FEATURE
<222> LOCATION: (3)..(3)
<223> OTHER INFORMATION: Xaa = Ser or D-Ser

<400> SEQUENCE: 10

Ser Xaa Xaa
1

<210> SEQ ID NO 11
<211> LENGTH: 3
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: MISC_FEATURE
<222> LOCATION: (2)..(2)
<223> OTHER INFORMATION: Xaa = D-Tyr
<220> FEATURE:
<221> NAME/KEY: MISC_FEATURE
<222> LOCATION: (3)..(3)
<223> OTHER INFORMATION: Xaa = D-Ser

<400> SEQUENCE: 11

Xaa Xaa Xaa
1

<210> SEQ ID NO 12
<211> LENGTH: 3
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = D-Tyr
<220> FEATURE:
<221> NAME/KEY: MISC_FEATURE
<222> LOCATION: (3)..(3)
<223> OTHER INFORMATION: Xaa = D-Ser

<400> SEQUENCE: 12

Lys Xaa Xaa
1

<210> SEQ ID NO 13
<211> LENGTH: 3
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = Pal
<220> FEATURE:
<221> NAME/KEY: MISC_FEATURE
<222> LOCATION: (2)..(2)
<223> OTHER INFORMATION: Xaa = D-Lys
<220> FEATURE:
<221> NAME/KEY: MISC_FEATURE
<222> LOCATION: (3)..(3)
<223> OTHER INFORMATION: Xaa = D-Ser

<400> SEQUENCE: 13

Xaa Xaa Xaa
1
```

```
<210> SEQ ID NO 14
<211> LENGTH: 3
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = D-Tyr
<220> FEATURE:
<221> NAME/KEY: MISC_FEATURE
<222> LOCATION: (3)..(3)
<223> OTHER INFORMATION: Xaa = D-Ser

<400> SEQUENCE: 14

Thr Xaa Xaa
1

<210> SEQ ID NO 15
<211> LENGTH: 7
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: Xaa = Gln, Asn, Nle, or Nva
<220> FEATURE:
<221> NAME/KEY: MISC_FEATURE
<222> LOCATION: (3)..(3)
<223> OTHER INFORMATION: Xaa = Ava, Gly, Leu, Val Ile, Nle, or Nva
<220> FEATURE:
<221> NAME/KEY: MISC_FEATURE
<222> LOCATION: (4)..(4)
<223> OTHER INFORMATION: Xaa = b-Ala, 4-amino butyric acid, Gly, Ala,
      D-Ala, N-Me-Ala
<220> FEATURE:
<221> NAME/KEY: MISC_FEATURE
<222> LOCATION: (6)..(6)
<223> OTHER INFORMATION: Xaa = Phe, Tyr, 4-Chloro-Phe, 4-Fluoro-Phe,
      4-Bromo-Phe, 4-NO2-Phe, Ala, Gly, Leu, Val, Ile, Nle, or Nva
<220> FEATURE:
<221> NAME/KEY: MISC_FEATURE
<222> LOCATION: (7)..(7)
<223> OTHER INFORMATION: Xaa = Met, Phe, Tyr, 4-Chloro-Phe,
      4-Fluoro-Phe, 4-Bromo-Phe, 4-NO2-Phe, Ala, Gly, Leu, Val, Ile,
      Nle, or Nva
<220> FEATURE:
<221> NAME/KEY: MOD_RES
<222> LOCATION: (7)..(7)
<223> OTHER INFORMATION: (amide or N-alkyl amide) attached to (lower
      alkyl amide) attached to (lower alkyl amide)

<400> SEQUENCE: 15

Xaa Trp Xaa Xaa His Xaa Xaa
1               5

<210> SEQ ID NO 16
<211> LENGTH: 12
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = D-Ser
<220> FEATURE:
<221> NAME/KEY: MISC_FEATURE
<222> LOCATION: (3)..(3)
<223> OTHER INFORMATION: Xaa = Nle
```

```
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (5)..(5)
<223> OTHER INFORMATION: Xaa = D-Ser
<220> FEATURE:
<221> NAME/KEY: MISC_FEATURE
<222> LOCATION: (8)..(8)
<223> OTHER INFORMATION: Xaa = D-Trp

<400> SEQUENCE: 16

Gly Xaa Xaa Xaa Xaa Cys Phe Xaa Lys Thr Cys Thr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = D-Ser
<220> FEATURE:
<221> NAME/KEY: MISC_FEATURE
<222> LOCATION: (3)..(3)
<223> OTHER INFORMATION: Xaa = Nle
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (5)..(5)
<223> OTHER INFORMATION: Xaa = D-Ser
<220> FEATURE:
<221> NAME/KEY: MOD_RES
<222> LOCATION: (6)..(11)
<223> OTHER INFORMATION: Cysteine at positions 6 and 11 are circularized
<220> FEATURE:
<221> NAME/KEY: MISC_FEATURE
<222> LOCATION: (8)..(8)
<223> OTHER INFORMATION: Xaa = D-Trp

<400> SEQUENCE: 17

Gly Xaa Xaa Xaa Xaa Cys Phe Xaa Lys Thr Cys Thr
1               5                   10

<210> SEQ ID NO 18
<211> LENGTH: 11
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = D-Ser
<220> FEATURE:
<221> NAME/KEY: MISC_FEATURE
<222> LOCATION: (3)..(3)
<223> OTHER INFORMATION: Xaa = D-Lys
<220> FEATURE:
<221> NAME/KEY: MISC_FEATURE
<222> LOCATION: (8)..(8)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = Nle
```

```
<400> SEQUENCE: 18

Gly Xaa Xaa Gln Trp Ala Val Xaa His Phe Xaa
1               5                   10

<210> SEQ ID NO 19
<211> LENGTH: 11
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = D-Ser
<220> FEATURE:
<221> NAME/KEY: MISC_FEATURE
<222> LOCATION: (3)..(3)
<223> OTHER INFORMATION: Xaa = D-Tyr
<220> FEATURE:
<221> NAME/KEY: MISC_FEATURE
<222> LOCATION: (8)..(8)
<223> OTHER INFORMATION: Xaa = beta-Ala
<220> FEATURE:
<221> NAME/KEY: MISC_FEATURE
<222> LOCATION: (11)..(11)
<223> OTHER INFORMATION: Xaa = Nle

<400> SEQUENCE: 19

Gly Xaa Xaa Gln Trp Ala Val Xaa His Phe Xaa
1               5                   10

<210> SEQ ID NO 20
<211> LENGTH: 15
<212> TYPE: PRT
<213> ORGANISM: Artificial Sequence
<220> FEATURE:
<223> OTHER INFORMATION: SYNTHETIC

<400> SEQUENCE: 20

His Leu Gln Ile Gln Pro Trp Tyr Pro Gln Ile Ser Gly Lys Ser
1               5                   10                  15

<210> SEQ ID NO 21
<211> LENGTH: 13
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Ser or D-Ser
<220> FEATURE:
<221> NAME/KEY: MISC_FEATURE
<222> LOCATION: (3)..(3)
<223> OTHER INFORMATION: Xaa = D-Ser
<220> FEATURE:
<221> NAME/KEY: MISC_FEATURE
<222> LOCATION: (4)..(4)
<223> OTHER INFORMATION: Xaa = Norleucine
<220> FEATURE:
<221> NAME/KEY: MISC_FEATURE
<222> LOCATION: (5)..(5)
<223> OTHER INFORMATION: Xaa = D-Tyr
<220> FEATURE:
<221> NAME/KEY: MISC_FEATURE
<222> LOCATION: (6)..(6)
<223> OTHER INFORMATION: Xaa = D-Ser
<220> FEATURE:
<221> NAME/KEY: MISC_FEATURE
<222> LOCATION: (9)..(9)
<223> OTHER INFORMATION: Xaa = D-Trp
```

```
<400> SEQUENCE: 21

Gly Xaa Xaa Xaa Xaa Xaa Cys Phe Xaa Lys Thr Cys Thr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = Ser or D-Ser
<220> FEATURE:
<221> NAME/KEY: MISC_FEATURE
<222> LOCATION: (3)..(3)
<223> OTHER INFORMATION: Xaa = D-Ser
<220> FEATURE:
<221> NAME/KEY: MISC_FEATURE
<222> LOCATION: (4)..(4)
<223> OTHER INFORMATION: Xaa = Norleucine
<220> FEATURE:
<221> NAME/KEY: MISC_FEATURE
<222> LOCATION: (5)..(5)
<223> OTHER INFORMATION: Xaa = D-Tyr
<220> FEATURE:
<221> NAME/KEY: MISC_FEATURE
<222> LOCATION: (6)..(6)
<223> OTHER INFORMATION: Xaa = D-Ser
<220> FEATURE:
<221> NAME/KEY: MOD_RES
<222> LOCATION: (7)..(12)
<223> OTHER INFORMATION: Circularized at positions 7 and 12
<220> FEATURE:
<221> NAME/KEY: MISC_FEATURE
<222> LOCATION: (9)..(9)
<223> OTHER INFORMATION: Xaa = D-Trp

<400> SEQUENCE: 22

Gly Xaa Xaa Xaa Xaa Xaa Cys Phe Xaa Lys Thr Cys Thr
1               5                   10

<210> SEQ ID NO 23
<211> LENGTH: 14
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(3)
<223> OTHER INFORMATION: Xaa = Ser or D-Ser
<220> FEATURE:
<221> NAME/KEY: MISC_FEATURE
<222> LOCATION: (4)..(4)
<223> OTHER INFORMATION: Xaa = D-Ser
<220> FEATURE:
<221> NAME/KEY: MISC_FEATURE
<222> LOCATION: (5)..(5)
<223> OTHER INFORMATION: Xaa = Norleucine
<220> FEATURE:
<221> NAME/KEY: MISC_FEATURE
<222> LOCATION: (6)..(6)
<223> OTHER INFORMATION: Xaa = D-Tyr
<220> FEATURE:
<221> NAME/KEY: MISC_FEATURE
<222> LOCATION: (7)..(7)
<223> OTHER INFORMATION: Xaa = D-Ser
<220> FEATURE:
<221> NAME/KEY: MISC_FEATURE
<222> LOCATION: (10)..(10)
<223> OTHER INFORMATION: Xaa = D-Trp

<400> SEQUENCE: 23
```

Gly Xaa Xaa Xaa Xaa Xaa Xaa Cys Phe Xaa Lys Thr Cys Thr
1               5                   10

<210> SEQ ID NO 24
<211> LENGTH: 15
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(4)
<223> OTHER INFORMATION: Xaa = Ser or D-Ser
<220> FEATURE:
<221> NAME/KEY: MISC_FEATURE
<222> LOCATION: (5)..(5)
<223> OTHER INFORMATION: Xaa = D-Ser
<220> FEATURE:
<221> NAME/KEY: MISC_FEATURE
<222> LOCATION: (6)..(6)
<223> OTHER INFORMATION: Xaa = Norleucine
<220> FEATURE:
<221> NAME/KEY: MISC_FEATURE
<222> LOCATION: (7)..(7)
<223> OTHER INFORMATION: Xaa = D-Tyr
<220> FEATURE:
<221> NAME/KEY: MISC_FEATURE
<222> LOCATION: (8)..(8)
<223> OTHER INFORMATION: Xaa = D-Ser
<220> FEATURE:
<221> NAME/KEY: MISC_FEATURE
<222> LOCATION: (11)..(11)
<223> OTHER INFORMATION: Xaa = D-Trp

<400> SEQUENCE: 24

Gly Xaa Xaa Xaa Xaa Xaa Xaa Xaa Cys Phe Xaa Lys Thr Cys Thr
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(5)
<223> OTHER INFORMATION: Xaa = Ser or D-Ser
<220> FEATURE:
<221> NAME/KEY: MISC_FEATURE
<222> LOCATION: (6)..(6)
<223> OTHER INFORMATION: Xaa = D-Ser
<220> FEATURE:
<221> NAME/KEY: MISC_FEATURE
<222> LOCATION: (7)..(7)
<223> OTHER INFORMATION: Xaa = Norleucine
<220> FEATURE:
<221> NAME/KEY: MISC_FEATURE
<222> LOCATION: (8)..(8)
<223> OTHER INFORMATION: Xaa = D-Tyr
<220> FEATURE:
<221> NAME/KEY: MISC_FEATURE
<222> LOCATION: (9)..(9)
<223> OTHER INFORMATION: Xaa = D-Ser
<220> FEATURE:
<221> NAME/KEY: MISC_FEATURE
<222> LOCATION: (12)..(12)
<223> OTHER INFORMATION: Xaa = D-Trp

<400> SEQUENCE: 25

Gly Xaa Xaa Xaa Xaa Xaa Xaa Xaa Xaa Cys Phe Xaa Lys Thr Cys Thr
1               5                   10                  15

```
<210> SEQ ID NO 26
<211> LENGTH: 17
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(6)
<223> OTHER INFORMATION: Xaa = Ser or D-Ser
<220> FEATURE:
<221> NAME/KEY: MISC_FEATURE
<222> LOCATION: (7)..(7)
<223> OTHER INFORMATION: Xaa = D-Ser
<220> FEATURE:
<221> NAME/KEY: MISC_FEATURE
<222> LOCATION: (8)..(8)
<223> OTHER INFORMATION: Xaa = Norleucine
<220> FEATURE:
<221> NAME/KEY: MISC_FEATURE
<222> LOCATION: (9)..(9)
<223> OTHER INFORMATION: Xaa = D-Tyr
<220> FEATURE:
<221> NAME/KEY: MISC_FEATURE
<222> LOCATION: (10)..(10)
<223> OTHER INFORMATION: Xaa = D-Ser
<220> FEATURE:
<221> NAME/KEY: MISC_FEATURE
<222> LOCATION: (13)..(13)
<223> OTHER INFORMATION: Xaa = D-Trp

<400> SEQUENCE: 26

Gly Xaa Xaa Xaa Xaa Xaa Xaa Xaa Xaa Xaa Cys Phe Xaa Lys Thr Cys
1               5                   10                  15

Thr

<210> SEQ ID NO 27
<211> LENGTH: 18
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(7)
<223> OTHER INFORMATION: Xaa =Ser or D-Ser
<220> FEATURE:
<221> NAME/KEY: MISC_FEATURE
<222> LOCATION: (8)..(8)
<223> OTHER INFORMATION: Xaa = D-Ser
<220> FEATURE:
<221> NAME/KEY: MISC_FEATURE
<222> LOCATION: (9)..(9)
<223> OTHER INFORMATION: Xaa = Norleucine
<220> FEATURE:
<221> NAME/KEY: MISC_FEATURE
<222> LOCATION: (10)..(10)
<223> OTHER INFORMATION: Xaa = D-Tyr
<220> FEATURE:
<221> NAME/KEY: MISC_FEATURE
<222> LOCATION: (11)..(11)
<223> OTHER INFORMATION: Xaa = D-Ser
<220> FEATURE:
<221> NAME/KEY: MISC_FEATURE
<222> LOCATION: (14)..(14)
<223> OTHER INFORMATION: Xaa = D-Trp

<400> SEQUENCE: 27

Gly Xaa Xaa Xaa Xaa Xaa Xaa Xaa Xaa Xaa Xaa Cys Phe Xaa Lys Thr
1               5                   10                  15

Cys Thr

<210> SEQ ID NO 28
```

```
<211> LENGTH: 19
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(8)
<223> OTHER INFORMATION: Xaa = Ser or D-Ser
<220> FEATURE:
<221> NAME/KEY: MISC_FEATURE
<222> LOCATION: (9)..(9)
<223> OTHER INFORMATION: Xaa = D-Ser
<220> FEATURE:
<221> NAME/KEY: MISC_FEATURE
<222> LOCATION: (10)..(10)
<223> OTHER INFORMATION: Xaa = Norleucine
<220> FEATURE:
<221> NAME/KEY: MISC_FEATURE
<222> LOCATION: (11)..(11)
<223> OTHER INFORMATION: Xaa = D-Tyr
<220> FEATURE:
<221> NAME/KEY: MISC_FEATURE
<222> LOCATION: (12)..(12)
<223> OTHER INFORMATION: Xaa = D-Ser
<220> FEATURE:
<221> NAME/KEY: MISC_FEATURE
<222> LOCATION: (15)..(15)
<223> OTHER INFORMATION: Xaa = D-Trp

<400> SEQUENCE: 28

Gly Xaa Xaa Xaa Xaa Xaa Xaa Xaa Xaa Xaa Xaa Xaa Cys Phe Xaa Lys
1               5                   10                  15

Thr Cys Thr

<210> SEQ ID NO 29
<211> LENGTH: 20
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(9)
<223> OTHER INFORMATION: Xaa = Ser or  D-Ser
<220> FEATURE:
<221> NAME/KEY: MISC_FEATURE
<222> LOCATION: (10)..(10)
<223> OTHER INFORMATION: Xaa = D-Ser
<220> FEATURE:
<221> NAME/KEY: MISC_FEATURE
<222> LOCATION: (11)..(11)
<223> OTHER INFORMATION: Xaa = Norleucine
<220> FEATURE:
<221> NAME/KEY: MISC_FEATURE
<222> LOCATION: (12)..(12)
<223> OTHER INFORMATION: Xaa = D-Tyr
<220> FEATURE:
<221> NAME/KEY: MISC_FEATURE
<222> LOCATION: (13)..(13)
<223> OTHER INFORMATION: Xaa = D-Ser
<220> FEATURE:
<221> NAME/KEY: MISC_FEATURE
<222> LOCATION: (16)..(16)
<223> OTHER INFORMATION: Xaa = D-Trp

<400> SEQUENCE: 29

Gly Xaa Xaa Xaa Xaa Xaa Xaa Xaa Xaa Xaa Xaa Xaa Xaa Cys Phe Xaa
1               5                   10                  15

Lys Thr Cys Thr
20

<210> SEQ ID NO 30
```

```
<211> LENGTH: 21
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(10)
<223> OTHER INFORMATION: Xaa = Ser or D-Ser
<220> FEATURE:
<221> NAME/KEY: MISC_FEATURE
<222> LOCATION: (11)..(11)
<223> OTHER INFORMATION: Xaa = D-Ser
<220> FEATURE:
<221> NAME/KEY: MISC_FEATURE
<222> LOCATION: (12)..(12)
<223> OTHER INFORMATION: Xaa = Norleucine
<220> FEATURE:
<221> NAME/KEY: MISC_FEATURE
<222> LOCATION: (13)..(13)
<223> OTHER INFORMATION: Xaa = D-Tyr
<220> FEATURE:
<221> NAME/KEY: MISC_FEATURE
<222> LOCATION: (14)..(14)
<223> OTHER INFORMATION: Xaa = D-Ser
<220> FEATURE:
<221> NAME/KEY: MISC_FEATURE
<222> LOCATION: (17)..(17)
<223> OTHER INFORMATION: Xaa = D-Trp

<400> SEQUENCE: 30

Gly Xaa Xaa Xaa Xaa Xaa Xaa Xaa Xaa Xaa Xaa Xaa Xaa Xaa Cys Phe
1               5                   10                  15

Xaa Lys Thr Cys Thr
            20

<210> SEQ ID NO 31
<211> LENGTH: 22
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(11)
<223> OTHER INFORMATION: Xaa = Ser or D-Ser
<220> FEATURE:
<221> NAME/KEY: MISC_FEATURE
<222> LOCATION: (12)..(12)
<223> OTHER INFORMATION: Xaa = D-Ser
<220> FEATURE:
<221> NAME/KEY: MISC_FEATURE
<222> LOCATION: (13)..(13)
<223> OTHER INFORMATION: Xaa = Norleucine
<220> FEATURE:
<221> NAME/KEY: MISC_FEATURE
<222> LOCATION: (14)..(14)
<223> OTHER INFORMATION: Xaa = D-Tyr
<220> FEATURE:
<221> NAME/KEY: MISC_FEATURE
<222> LOCATION: (15)..(15)
<223> OTHER INFORMATION: Xaa = D-Ser
<220> FEATURE:
<221> NAME/KEY: MISC_FEATURE
<222> LOCATION: (18)..(18)
<223> OTHER INFORMATION: Xaa = D-Trp

<400> SEQUENCE: 31

Gly Xaa Xaa Xaa Xaa Xaa Xaa Xaa Xaa Xaa Xaa Xaa Xaa Xaa Cys
1               5                   10                  15

Phe Xaa Lys Thr Cys Thr
            20
```

```
<210> SEQ ID NO 32
<211> LENGTH: 23
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(12)
<223> OTHER INFORMATION: Xaa = Ser or D-Ser
<220> FEATURE:
<221> NAME/KEY: MISC_FEATURE
<222> LOCATION: (13)..(13)
<223> OTHER INFORMATION: Xaa = D-Ser
<220> FEATURE:
<221> NAME/KEY: MISC_FEATURE
<222> LOCATION: (14)..(14)
<223> OTHER INFORMATION: Xaa = Norleucine
<220> FEATURE:
<221> NAME/KEY: MISC_FEATURE
<222> LOCATION: (15)..(15)
<223> OTHER INFORMATION: Xaa = D-Tyr
<220> FEATURE:
<221> NAME/KEY: MISC_FEATURE
<222> LOCATION: (16)..(16)
<223> OTHER INFORMATION: Xaa = D-Ser
<220> FEATURE:
<221> NAME/KEY: MISC_FEATURE
<222> LOCATION: (19)..(19)
<223> OTHER INFORMATION: Xaa = D-Trp

<400> SEQUENCE: 32

Gly Xaa Xaa Xaa Xaa Xaa Xaa Xaa Xaa Xaa Xaa Xaa Xaa Xaa Xaa
1               5                   10                  15

Cys Phe Xaa Lys Thr Cys Thr
            20

<210> SEQ ID NO 33
<211> LENGTH: 24
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(13)
<223> OTHER INFORMATION: Xaa = Ser or D-Ser
<220> FEATURE:
<221> NAME/KEY: MISC_FEATURE
<222> LOCATION: (14)..(14)
<223> OTHER INFORMATION: Xaa = D-Ser
<220> FEATURE:
<221> NAME/KEY: MISC_FEATURE
<222> LOCATION: (15)..(15)
<223> OTHER INFORMATION: Xaa = Norleucine
<220> FEATURE:
<221> NAME/KEY: MISC_FEATURE
<222> LOCATION: (16)..(16)
<223> OTHER INFORMATION: Xaa = D-Tyr
<220> FEATURE:
<221> NAME/KEY: MISC_FEATURE
<222> LOCATION: (17)..(17)
<223> OTHER INFORMATION: Xaa = D-Ser
<220> FEATURE:
<221> NAME/KEY: MISC_FEATURE
<222> LOCATION: (20)..(20)
<223> OTHER INFORMATION: Xaa = D-Trp

<400> SEQUENCE: 33

Gly Xaa Xaa Xaa Xaa Xaa Xaa Xaa Xaa Xaa Xaa Xaa Xaa Xaa Xaa
1               5                   10                  15

Xaa Cys Phe Xaa Lys Thr Cys Thr
                20
```

<210> SEQ ID NO 34
<211> LENGTH: 25
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(14)
<223> OTHER INFORMATION: Xaa = Ser or D-Ser
<220> FEATURE:
<221> NAME/KEY: MISC_FEATURE
<222> LOCATION: (15)..(15)
<223> OTHER INFORMATION: Xaa = D-Ser
<220> FEATURE:
<221> NAME/KEY: MISC_FEATURE
<222> LOCATION: (16)..(16)
<223> OTHER INFORMATION: Xaa = Norleucine
<220> FEATURE:
<221> NAME/KEY: MISC_FEATURE
<222> LOCATION: (17)..(17)
<223> OTHER INFORMATION: Xaa = D-Tyr
<220> FEATURE:
<221> NAME/KEY: MISC_FEATURE
<222> LOCATION: (18)..(18)
<223> OTHER INFORMATION: Xaa = D-Ser
<220> FEATURE:
<221> NAME/KEY: MISC_FEATURE
<222> LOCATION: (21)..(21)
<223> OTHER INFORMATION: Xaa = D-Trp

<400> SEQUENCE: 34

Gly Xaa Xaa Xaa Xaa Xaa Xaa Xaa Xaa Xaa Xaa Xaa Xaa Xaa Xaa
1               5                   10                  15

Xaa Xaa Cys Phe Xaa Lys Thr Cys Thr
            20                  25

<210> SEQ ID NO 35
<211> LENGTH: 26
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(15)
<223> OTHER INFORMATION: Xaa = Ser or D-Ser
<220> FEATURE:
<221> NAME/KEY: MISC_FEATURE
<222> LOCATION: (16)..(16)
<223> OTHER INFORMATION: Xaa = D-Ser
<220> FEATURE:
<221> NAME/KEY: MISC_FEATURE
<222> LOCATION: (17)..(17)
<223> OTHER INFORMATION: Xaa = Norleucine
<220> FEATURE:
<221> NAME/KEY: MISC_FEATURE
<222> LOCATION: (18)..(18)
<223> OTHER INFORMATION: Xaa = D-Tyr
<220> FEATURE:
<221> NAME/KEY: MISC_FEATURE
<222> LOCATION: (19)..(19)
<223> OTHER INFORMATION: Xaa = D-Ser
<220> FEATURE:
<221> NAME/KEY: MISC_FEATURE
<222> LOCATION: (22)..(22)
<223> OTHER INFORMATION: Xaa = D-Trp

<400> SEQUENCE: 35

Gly Xaa Xaa Xaa Xaa Xaa Xaa Xaa Xaa Xaa Xaa Xaa Xaa Xaa Xaa
1               5                   10                  15

Xaa Xaa Xaa Cys Phe Xaa Lys Thr Cys Thr
            20                  25

```
<210> SEQ ID NO 36
<211> LENGTH: 27
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(16)
<223> OTHER INFORMATION: Xaa = Ser or D-Ser
<220> FEATURE:
<221> NAME/KEY: MISC_FEATURE
<222> LOCATION: (17)..(17)
<223> OTHER INFORMATION: Xaa = D-Ser
<220> FEATURE:
<221> NAME/KEY: MISC_FEATURE
<222> LOCATION: (18)..(18)
<223> OTHER INFORMATION: Xaa = Norleucine
<220> FEATURE:
<221> NAME/KEY: MISC_FEATURE
<222> LOCATION: (19)..(19)
<223> OTHER INFORMATION: Xaa = D-Tyr
<220> FEATURE:
<221> NAME/KEY: MISC_FEATURE
<222> LOCATION: (20)..(20)
<223> OTHER INFORMATION: Xaa = D-Ser
<220> FEATURE:
<221> NAME/KEY: MISC_FEATURE
<222> LOCATION: (23)..(23)
<223> OTHER INFORMATION: Xaa = D-Trp

<400> SEQUENCE: 36

Gly Xaa Xaa Xaa Xaa Xaa Xaa Xaa Xaa Xaa Xaa Xaa Xaa Xaa Xaa
1               5                   10                  15

Xaa Xaa Xaa Xaa Cys Phe Xaa Lys Thr Cys Thr
        20                  25

<210> SEQ ID NO 37
<211> LENGTH: 6
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (3)..(3)
<223> OTHER INFORMATION: Xaa = D-Trp

<400> SEQUENCE: 37

Cys Phe Xaa Lys Thr Cys
1               5

<210> SEQ ID NO 38
<211> LENGTH: 6
<212> TYPE: PRT
<213> ORGANISM: Artificial Sequence
<220> FEATURE:
<223> OTHER INFORMATION: SYNTHETIC
<220> FEATURE:
<221> NAME/KEY: MOD_RES
<222> LOCATION: (1)..(6)
<223> OTHER INFORMATION: Cysteines at positions 1 and 6 are Circularized
<220> FEATURE:
<221> NAME/KEY: MISC_FEATURE
<222> LOCATION: (3)..(3)
<223> OTHER INFORMATION: Xaa = D-Trp

<400> SEQUENCE: 38

Cys Phe Xaa Lys Thr Cys
1               5
```

```
<210> SEQ ID NO 39
<211> LENGTH: 12
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = D-Ser
<220> FEATURE:
<221> NAME/KEY: MISC_FEATURE
<222> LOCATION: (3)..(3)
<223> OTHER INFORMATION: Xaa = Norleucine
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (5)..(5)
<223> OTHER INFORMATION: Xaa = D-Ser
<220> FEATURE:
<221> NAME/KEY: MISC_FEATURE
<222> LOCATION: (8)..(8)
<223> OTHER INFORMATION: Xaa = D-Trp

<400> SEQUENCE: 39

Gly Xaa Xaa Xaa Xaa Cys Phe Xaa Lys Thr Cys Thr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: Xaa = D-Ser
<220> FEATURE:
<221> NAME/KEY: MISC_FEATURE
<222> LOCATION: (3)..(3)
<223> OTHER INFORMATION: Xaa = Nle
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (5)..(5)
<223> OTHER INFORMATION: Xaa = D-Ser
<220> FEATURE:
<221> NAME/KEY: MOD_RES
<222> LOCATION: (6)..(11)
<223> OTHER INFORMATION: Cysteine at positions 6 and 11 are circularized
<220> FEATURE:
<221> NAME/KEY: MISC_FEATURE
<222> LOCATION: (8)..(8)
<223> OTHER INFORMATION: Xaa = D-Trp

<400> SEQUENCE: 40

Gly Xaa Xaa Xaa Xaa Cys Phe Xaa Lys Thr Cys Thr
1               5                   10

<210> SEQ ID NO 41
<211> LENGTH: 4
<212> TYPE: PRT
<213> ORGANISM: Artificial Sequence
<220> FEATURE:
<223> OTHER INFORMATION: SYNTHETIC

<400> SEQUENCE: 41
```

```
Met Leu Phe Lys
1

<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Tyr Ile Gly Ser Arg
1               5

<210> SEQ ID NO 43
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: MISC_FEATURE
<222> LOCATION: (2)..(2)
<223> OTHER INFORMATION: Xaa = D-Tyr
<220> FEATURE:
<221> NAME/KEY: MISC_FEATURE
<222> LOCATION: (3)..(3)
<223> OTHER INFORMATION: Xaa = D-Ser
<220> FEATURE:
<221> NAME/KEY: MISC_FEATURE
<222> LOCATION: (6)..(6)
<223> OTHER INFORMATION: Xaa = D-Trp

<400> SEQUENCE: 43

Xaa Xaa Xaa Cys Phe Xaa Lys Thr Cys Thr
1               5                   10

<210> SEQ ID NO 44
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa= Nle
<220> FEATURE:
<221> NAME/KEY: MISC_FEATURE
<222> LOCATION: (2)..(2)
<223> OTHER INFORMATION: Xaa = D-Tyr
<220> FEATURE:
<221> NAME/KEY: MISC_FEATURE
<222> LOCATION: (3)..(3)
<223> OTHER INFORMATION: Xaa = D-Ser
<220> FEATURE:
<221> NAME/KEY: MOD_RES
<222> LOCATION: (4)..(9)
<223> OTHER INFORMATION: Cysteine at positions 4 and 9 are circularized
<220> FEATURE:
<221> NAME/KEY: MISC_FEATURE
<222> LOCATION: (6)..(6)
<223> OTHER INFORMATION: Xaa = D-Trp

<400> SEQUENCE: 44

Xaa Xaa Xaa Cys Phe Xaa Lys Thr Cys Thr
1               5                   10
```

```
<210> SEQ ID NO 45
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = D-Lys, D-Tyr, D-Ser, L-Ser or is deleted
<220> FEATURE:
<221> NAME/KEY: MISC_FEATURE
<222> LOCATION: (2)..(2)
<223> OTHER INFORMATION: Xaa = D-Lys, D-Tyr, or is deleted
<220> FEATURE:
<221> NAME/KEY: MISC_FEATURE
<222> LOCATION: (3)..(3)
<223> OTHER INFORMATION: Xaa = Lys, Ser, hSer, Thr, Nle, Abu, Nva, (2,
      3, or 4_3-pyridyl-Ala (Pal), Orn, Dab, Dap, 4-NH2-Phe, D-4-OH-Pro,
      L-4-OH-Pro, or is deleted
<220> FEATURE:
<221> NAME/KEY: MISC_FEATURE
<222> LOCATION: (4)..(4)
<223> OTHER INFORMATION: Xaa = D-Lys, D-Tyr, D-Ser, D-4-OH-Pro,
      L-4-OH-Pro, 3-iodo-D-Tyr, 3-5 diiodo-D-Tyr, 3-astatine-D-Tyr,
      3-5 astatine-D-Tyr, 3-bromo-D-Tyr, 3-5 dibromo-D-Tyr, D-Asn,
      L-Asn, D-Asp, L-Asp, D-Glu, L-Glu, D-Gln, or L-Gln
<220> FEATURE:
<221> NAME/KEY: MISC_FEATURE
<222> LOCATION: (5)..(5)
<223> OTHER INFORMATION: Xaa = D-Lys, D-Tyr, D-Ser, L-Ser, D-4-OH-Pro,
      L-4-OH-Pro, 3-iodo-D-Tyr, 3-5 diiodo-D-Tyr, 3-astatine-D-Tyr, 3-5
      astatine-D-Tyr, 3-bromo-D-Tyr, 3-5 dibromo-D-Tyr, D-Asn, L-Asn,
      D-Asp, L-Asp, D-Glu, L-Glu, D-Gln, or L-Gln

<400> SEQUENCE: 45

Xaa Xaa Xaa Xaa Xaa
1               5

<210> SEQ ID NO 46
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(2)
<223> OTHER INFORMATION: Xaa = D-Tyr
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (5)..(5)
<223> OTHER INFORMATION: Xaa = D-Tyr, D-Ser, L-Ser, D-4-OH-Pro,
      L-4-OH-Pro, 3-iodo-D-Tyr, 3-5 diiodo-D-Tyr, 3-astatine-D-Tyr,
      3-5 astatine-D-Tyr, 3-bromo-D-Tyr, 3-5 dibromo-D-Tyr, D-Asn,
      L-Asn, D-Asp, L-Asp, D-Glu, L-Glu, D-Gln, or L-Gln

<400> SEQUENCE: 46

Xaa Xaa Lys Xaa Xaa
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: Xaa =  D- Lys
<220> FEATURE:
<221> NAME/KEY: MISC_FEATURE
<222> LOCATION: (2)..(2)
<223> OTHER INFORMATION: Xaa =  D-Tyr
<220> FEATURE:
<221> NAME/KEY: MISC_FEATURE
<222> LOCATION: (4)..(4)
<223> OTHER INFORMATION: Xaa =  D-Tyr
<220> FEATURE:
<221> NAME/KEY: MISC_FEATURE
<222> LOCATION: (5)..(5)
<223> OTHER INFORMATION: Xaa =  D-Ser, L-Ser, D-4-OH-Pro, L-4-OH-Pro,
     3-iodo-D-Tyr, 3-5 diiodo-D-Tyr, 3-astatine-D-Tyr, 3-5
     astatine-D-Tyr, 3-bromo-D-Tyr, 3-5 dibromo-D-Tyr, D-Asn, L-Asn,
     D-Asp, L-Asp, D-Glu, L-Glu, D-Gln, or L-Gln

<400> SEQUENCE: 47

Xaa Xaa Lys Xaa Xaa
1               5

<210> SEQ ID NO 48
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(2)
<223> OTHER INFORMATION: Xaa = absent
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (5)..(5)
<223> OTHER INFORMATION: Xaa = D-Ser, L-Ser, D-4-OH-Pro, L-4-OH-Pro,
     3-iodo-D-Tyr, 3-5 diiodo-D-Tyr, 3-astatine-D-Tyr, 3-5
     astatine-D-Tyr, 3-bromo-D-Tyr, 3-5 dibromo-D-Tyr, D-Asn, L-Asn,
     D-Asp, L-Asp, D-Glu, L-Glu, D-Gln, or L-Gln

<400> SEQUENCE: 48

Xaa Xaa Lys Xaa Xaa
1               5
```